United States Patent [19]

Maratos-Flier

[11] Patent Number: 5,849,708
[45] Date of Patent: Dec. 15, 1998

[54] PROMOTION OF EATING BEHAVIOR

[75] Inventor: Eleftheria Maratos-Flier, Newton, Mass.

[73] Assignee: Joslin Diabetes Center, Inc., Boston, Mass.

[21] Appl. No.: 473,022

[22] Filed: Jun. 6, 1995

[51] Int. Cl.⁶ .................................................. A61K 38/00
[52] U.S. Cl. ........................... 514/13; 530/300; 530/317
[58] Field of Search .................................. 530/300, 350, 530/317; 514/12, 14, 13

[56] References Cited

U.S. PATENT DOCUMENTS

| | | | |
|---|---|---|---|
| 5,049,655 | 9/1991 | Vaughan et al. | 530/326 |
| 5,210,076 | 5/1993 | Berliner et al. | 514/21 |
| 5,449,766 | 9/1995 | Vaughan et al. | 536/23.5 |
| 5,530,095 | 6/1996 | Vaughn et al. | 530/326 |

OTHER PUBLICATIONS

Lewin et al Science 237:1570, 1987.
Reeck Cell 50:667, Aug. 1987.
Presse et al Neuroscience vol. 71 No. 3 735–745, 1996.
Rossi et al Endinocrinology vol. 138 No. 1 351, 1997.
Qu et al Nature vol. 380 243, Mar. 1996.
Nahon, "The malanin–concentrating hormone: from the peptide to the gene" Crit. Rev. in Neurobiology 8(4):221–262 (1994).
Baile et al., "Role of Cholecystokinin and Opioid Peptides in Control of Food Intake," *Physiol. Reviews*, vol. 66, No. 1, 172–234 (1986).
Baker, B., "Melanin–concentrating Hormone Updated, Functional Considerations," TEM, vol. 5, No. 3, 120–126 (1994).
Bray, GA, "1989 McCollum Award Lecture. Genetic and Hypothalamic Mechanisms for Obesity–Finding the Needle in the Haystack," *Am J. Clin. Nutr.*, vol. 50, 891–902 (1989).
Bresson et al., "Donnees Ontogenetiques sur la Population d'interneurones Peptidergiques a Immunoreactivite de Type GRF₃₇ de L'hypothalamus Postero–Lateral Humain. Etudes Immunocytochimiques a L'aide d'un IS Anti–GRF₃₇ et d'un IS Anti–MCH (melanin–concentrating hormone)," *CR Soc. Biol.*, vol. 181, 376–382 (1987); A Abstract, Only.
Breton et al., "Structure and Regulation of the Mouse Melanin–Concentrating Hormone mRNA and Gene," *Molecular and Cellular Neurosciences*, vol. 4, 271–284 (1993).
Castrucci et al., "A Teleost Skin Bioassay for Melanotropic Peptides," *Gen. Comp. Endocrinol.*, vol. 66, 374–380 (1987).
Castrucci et al., "α–Melanotropin: The Minimal Active Sequence in the Lizard Skin Bioassay," *Gen. Comp. Endocrinol.*, vol. 73, 157–163 (1989).
Drozdz, R. and Eberle, A., "Binding Sites for Melanin–Concentrating Hormone (MCH) in Brain Synaptosomes and Membranes From Peripheral Tissues Identified with Highly Tritiated MCH," *J. of Receptor and Signal Transduction Research*, vol. 15(1–4), 487–502 (1995).

Drozdz, R. and Eberle, A., "Synthesis and Iodination of Human (Phenylalanine ¹³ Tyrosine ¹⁹) Melanin–concentrating Hormone for Radioreceptor Assay," *Journal of Peptide Science*, 23rd European Peptide Symposium, Braga, Portugal, vol. 1, 55–65 (1994).
Griffond et al., "The Synthesis of Melanin–concentrating Hormone is Stimulated by Ventromedial Hypothalamic Lesions in the Rat Lateral Hypothalamus: A Time–course Study," *Neuropeptides*, vol. 28, 267–275 (1995).
Hadley et al., "Differential Structural Requirements for the MSH and MCH Activities of Melanin Concentrating Hormone," *Life Sci.*, vol. 40, 1139–1145 (1987).
Hogben, L. and Slome, D., "The Pigmentary Effector System. VI. The Dual Character of Endocrine Co–ordination in Amphibian Colour Change," *Proc. Roy. Soc.*, B, vol. 108, 10–53 (1931).
Hruby et al., "α–Melanotropin: The Minimal Active Sequence in the Frog Skin Bioassay," *J. Med. Chem.*, vol. 30, 2126–2130 (1987).
Kawauchi et al., "Characterization of Melanin–concentrating Hormone in Chum Salmon Pituitaries," *Nature*, vol. 305, 321–323 (1983).
Kawauchi, H. and Kawazoe, I., "Structure–activity Studies on Melanin–concentrating Hormone," *Advances in Pigment Cell Res.*, 517–525 (1988).
Lebl et al., "Melanin Concentrating Hormone Analogues: Contration of the Cyclic Structure 1. Agonist Activity," *J. Med. Chem.*, vol. 31, 949–954 (1988).
Lebl et al., "Melanin Concentrating Hormone Analogues: Contraction of the Cyclic Structure. II. Antagonist Activity," *Life Sci.*, vol. 44, 451–457 (1989).
Liang, P. and Pardee, A., "Differential Display of Eukaryotic Messenger RNA by Means of the Polymerase Chain Reaction," *Science*, vol. 257, 967–971 (1992).
Matsunaga et al., "Melanin Concentrating Hormone (MCH): Synthesis and Bioactivity Studies of MCH Fragment Analogues," *Peptides*, vol. 10, 349–354 (1989).
Matsunaga et al., "Synthesis and Bioactivity Studies of Two Isosteric Acyclic Analogues of Melanin Concentrating Hormone," *Life Sci.*, vol. 51, 679–685 (1992).
Morley, J., "Neuropeptide Regulation of Appetite and Weight," *Endocrin. Rev.*, vol. 8, No. 3, 256–87 (1987).
Nahon et al., "Structure and Regulation of the Melanin–Concentrating Hormone Geneᵃ," *Ann. NY Acad. Sci.*, vol. 680, 111–129 (1993).
Naito et al., "Melanin–concentrating Hormone–like Immunoreactive Material in the Rat Hypothalamus; Characterization and Subcellular Localization," *Cell Tissue Res.*, vol. 253, 291–295 (1988).

(List continued on next page.)

*Primary Examiner*—Lila Feisee
*Assistant Examiner*—Julie E. Reeves
*Attorney, Agent, or Firm*—Fish & Richardson P.C.

[57] ABSTRACT

A method for promoting eating, the gain of weight or maintenance of weight in a subject. The method includes administering to the subject an effective amount of melanocyte concentrating hormone (MCH) or agonist thereof.

16 Claims, 2 Drawing Sheets

OTHER PUBLICATIONS

Parkes et al., "Secretion of Melanin–concentrating Hormone and Neuropeptide–El from Cultured Rat Hypothalmic Cells," *Endocrinology*, vol. 131, No. 4, 1826–1831 (1992).

Pesonen et al., "Hypothalamic Neuropeptide Expression After Food Restriction in Zucker Rats: Evidence of Persistent Neuropeptide Y Gene Activation," *Molecular Brain Research*, vol. 16, 255–260 (1992).

Sanacora et al., "Increased Hypothalamic Content of Preproneuropeptide Y Messenger Ribonucleic Acid in Genetically Obese Zucker Rats and Its Regulation by Food Deprivation," *Endocrinology*, vol. 127, No. 2, 730–736 (1990).

Skofitsch et al., "Immunohistochemical Localization or a Melanin Concentrating Hormone–Like Peptide in the Rat Brain," *Brain Research Bulletin*, vol. 15, 635–649 (1985).

Stanley et al., "Repeated Hypothalamic Stimulation with Neuropeptide Y Increases Daily Carbohydrate and Fat Intake and Body Weight Gain in Female Rats," *Physiol. and Behav.*, vol. 46, 173–177 (1989).

Tsujii et al., "GABA–related Feeding Control in Genetically Obese Rats," *Brain Research*, vol. 540, 48–54 (1991).

Wilding et al., "Increased Neuropeptide Y Content in Individual Hypothalmic Nuclei, but not Neuropeptide Y mRNA, in Diet–induced Obesity in Rats," *J. Endocrinol.*, vol. 132, 299–304 (1992).

Wilding et al., "Increased Neuropeptide–Y Messenger Ribonucleic Acid (mRNA) and Decreased Neurotensin mRNA in the Hypothalamus of the Obese (ob/ob) Mouse," *Endocrinology*, vol. 132, No. 5, 1939–1944 (1993).

Williams et al., "Hypothalamic Regulatory Peptides in Obese and Lean Zucker Rats," *Clinical Science*, vol. 80, 419–426 (1991).

Zamir et al., "Melanin–concentrating Hormone: Unique Peptide Neuronal System in the Rat Brain and Pituitary Gland," *Proc. Natl. Acad. Sci. USA*, vol. 83, 1528–1531 (1986).

Zhang et al., "Positional Cloning of the Mouse Obese Gene and its Human Homologue," *Nature*, vol. 372, 425–432 (1994).

PROMOTION OF EATING BEHAVIOR

BACKGROUND OF THE INVENTION

The invention relates to MCH, MCH agonists and antagonists, and their use to regulate eating behavior.

Although our understanding of rodent obesity has increased significantly through molecular analysis of obese mouse models, e.g., the ob/ob mouse, agouti mouse and brown adipose tissue deficient mouse models, the mechanism by which various molecular defects lead to altered feeding behavior remain largely unknown. In general, the molecular causes of hyperphagia and obesity in both man and animals are poorly understood (Bray (1989) *Am. J. Clin. Nutr.* 891–902). Recently two obesity related genes have been identified using positional cloning (Zhang et al. (1994) *Nature* 372:425–432).

Neurotransmitters and neuropeptides are known to affect feeding behavior. The neurotransmitters, serotonin and norepinephrine (NE) are involved in regulation of appetite, with serotonin agonists inhibiting appetite while NE agonists induce eating. Abnormal responses to the neurotransmitter GABA have also been reported (Tsuji et al. (1991) *Brain Research* 48–54. In addition, a number of neuropeptides have been implicated in regulating food intake. Neuropeptide Y (NPY) mimics the action of NE in the central nervous system. Injection of NPY induces feeding behavior in sated rats (Stanley et al. (1989) *Physiol and Behav.* 46:173–177) and levels of NPY and preproNPY mRNA may be altered in obese rodents, however, the results reported from different investigators has not been consistent. Increased levels of NPY are seen in the hypothalamus of Wistar rats with diet-induced obesity, although mRNA levels are unchanged (Wilding et al. (1992) *J. Endocrinol.* 132–299 404). In Zucker rats, NPY increased levels of hypothalamic NPY and preproNPY mRNA have been reported (Sanacor et al. (1990) *Endocrinology* 127:730–736; Pesonen et al. (1992) 255–260; and Williams et al. (1991) *Clincial Science* 80:419–426). In the same model, other investigators have found NPY levels unchanged, in the basal state, but increasing with food restrictions (Williams et al. (1991) *Clincial Science* 80:419–426). In ob/ob mice, hypothalamic NPY concentrations are unchanged, however, food restriction activates NPY gene expression (Wilding et al. (1993) *Endocrinology* 132:1939–1943). A number of other peptides including galanin, beta-endorphin, dynorphin, act to stimulate food intake in satiated rats when injected into the paraventricular nucleus or ventromedian nucleus. Factors derived from the gastrointestinal tract may also be important in appetite regulation. For example, cholecystokinin and bombesin inhibit food intake when injected into rats (Baile et al. (1986) *Physiol Reviews* 66:172–234 and Morley (1987) *Endocrinol Rev.* 8:256–87).

The presence of melanocyte concentrating hormone (MCH), a cyclic peptide, in fish hypothalamus was described over a decade ago. The role of MCH, in teleost fish appears to be regulation of color change; MCH induces melanophore aggregation and MSH induces melanophore dispersion (Nahon et al. (1993) *Ann. NY Acad. Sci.* 680:111–129). In 1985, immunoreactive MCH was also found in rodent brain (Skofitsch et al. (1985) *Brain Res. Bull.* 15:635–639), and it's subcellular localization in the rats and man was described a few years later (Naito et al. (1988) *Cell Tissue Res.* 253:291–295 and Bresson et al. (1987) *CR Soc Biol.* 181:376–382). In mammals, MCH gene expression is localized to the ventral aspect of the Zona Incerta and the lateral hypothalamus (Breton et al. (1993) *Molecular and Cellular Neurosciences* 4:271–284). The gene encodes an MCH peptide, as well as, a 13 amino acid peptide which is processed and released by hypothalamic cells in culture (Parkes et al (1992) *Endocrinology* 131:1826–1831). MCH perikarya project throughout the mammalian brain, and it is likely that MCH is involved in integrative processes which accompany complex behaviors (Skofitch et al. (1985) *Brain Res. Bull.* 15:635–639) (Zhang et al. (1994) *Nature* 372:425–432).

SUMMARY OF THE INVENTION

In general, the invention features, a method of promoting eating, appetite, or the gain or maintenance of weight, in a subject including: administering an effective amount of MCH, or an agonist or fragment thereof, to the subject.

In preferred embodiments: the subject is a mammal, e.g., a human; the subject is underweight or exhibits less than normal eating behavior; the subject suffers from an immune system disorder, e.g. AIDS, or is HIV positive; the subject suffers from anorexia nervosa, or renal disease, e.g., chronic renal disease or renal disease requiring dialysis; the subject is, has been, or will be, administered a treatment which results in decreased appetite or eating behavior or in a loss of weight, e.g., chemotherapy, radiation therapy, or dialysis.

In preferred embodiments, the method further includes diagnosing the subject as being at risk for: a disorder or unwanted condition related to MCH metabolism; an eating, appetite, or weight-related disorder; less than normal eating behavior; wasting; or being underweight.

In preferred embodiments, the method further includes repeating the administration of MCH, or an agonist, or a fragment thereof.

In preferred embodiments, the method further includes administering a treatment which results in decreased eating behavior or in a loss of weight, e.g., chemotherapy, radiation therapy, or dialysis. The treatment can be administered before, after, or during MCH or MCH agonist or fragment administration.

In preferred embodiments: the subject is a non-human animal, e.g., a non-human mammal, e.g., a non-human primate, a dog, or a rodent, e.g., a rat or a mouse; the subject is other than a fish. The subject can be wild type with respect to genes which condition weight or eating behavior, or the subject can carry one or more genetic lesions which affect weight or eating behavior. For example, the subject can carry a mutation in the ob gene, the MCH gene, or the ob receptor gene. The subject can be a transgenic animal, e.g., a transgenic which misexpresses the ob transgene, the MCH transgene, or the ob receptor transgene. The subject can also be deficient for brown fat tissue. E.g., a brown fat tissue "knockout" mouse can be made by fusing diphtheria toxin to a brown fat-specific promoter.

The administration of MCH or an MCH agonist or fragment can be initiated: when the recipient begins to show signs of insufficient eating, loss of appetite, or loss of weight, e.g., as evidenced by a decline weight of more than 10, 20, or 30% in body weight or when the subject is 10, 20, or 30% below normal body weight; when a loss in appetite is diagnosed; at the time a treatment which inhibits eating, appetite, or weight gain or maintenance, is begun or begins to exert its effects; or generally, as is needed to maintain health or appropriate weight levels.

The period over which the agent is administered (or the period over which clinically effective levels are maintained in the subject) can be long term, e.g., for six months or more or a year or more, or short term, e.g., for less than a year, more preferably six months or less, more preferably one month or less, and more preferably two weeks or less.

In another aspect, the invention features, a method of inhibiting eating, inhibiting appetite, or promoting the loss of weight, in a subject including: administering an effective amount of an antagonist of MCH to the subject.

In preferred embodiments: the subject is a mammal, e.g., a human; the subject is overweight or exhibits compulsive or other unwanted eating behavior; the subject is, has been, or will be, administered a treatment which results in increased eating behavior, e.g., steroid therapy.

In preferred embodiments, the method further includes diagnosing the subject as being at risk for any of: a disorder or unwanted condition related to MCH metabolism; an eating or weight-related disorder; compulsive or other unwanted eating behavior, obesity; or other eating or weight related disorder.

In preferred embodiments, the method further includes repeating the administration of an MCH antagonist.

In preferred embodiments, the method further includes administering a treatment which results in increased eating behavior or in a gain of weight, e.g., steroid therapy The treatment can be administered before, after, or during MCH antagonist.

In preferred embodiments: the subject is a non-human animal, e.g., a non-human mammal, e.g., a non-human primate, dog, or a rodent, e.g., a rat or a mouse; the subject is other than a fish. The subject can be wild type with respect to genes which condition weight or eating behavior, or the subject can carry one or more genetic lesions which affect weight or eating behavior. For example, the subject can carry a mutation in the ob gene, the MCH gene, or the ob receptor gene. The subject can be a transgenic animal, e.g., a transgenic which misexpresses the ob transgene, the MCH transgene, or the ob receptor transgene. The subject can also be deficient for brown fat tissue. E.g., a brown fat tissue "knockout" mouse can be made by fusing diphtheria toxin to a brown fat-specific promoter.

In preferred embodiments, the antagonist is a peptide analog of MCH having at least 50, 60, 70, 80, or 90% homology with MCH.

The administration of an MCH antagonist can be initiated: when the recipient begins to show signs of unwanted eating behavior or gain in weight, e.g., as evidenced by an increase of more than 10, 20, or 30% in body weight or when the subject is 10, 20, or 30% above normal body weight; when an increase in appetite is diagnosed; at the time a treatment which promotes eating, appetite, or weight gain or maintenance, is begun or begins to exert its effects; or generally, as is needed to maintain health or acceptable weight levels.

The period over which the agent is administered (or the period over which clinically effective levels are maintained in the subject) can be long term, e.g., for six months or more or a year or more, or short term, e.g., for less than a year, more preferably six months or less, more preferably one month or less, and more preferably two weeks or less.

The inventor has discovered that MCH induces eating behavior. The invention includes a number of methods for evaluating treatments or agents for MCH agonist or antagonist activity. Some methods use in vitro assays, while others use cells, and yet others use animals. Methods referred to herein can be used individually, or in combination, to evaluate agents for MCH agonist or antagonist activity. For example, relatively rapid in vitro or cell based assays can be used as an initial screen and an animal assay used as a secondary screen.

The treatment can be any treatment which can result in the desired effect but the administration of agents, e.g., drugs or chemicals, is preferred. Preferably, the treatment is other than surgical intervention, e.g., the production of surgical lesions, e.g., electrolytic lesions, e.g., the treatment is other than a ventromedial hypothalmic lesion, e.g., an electrolytically produced ventromedial hypothalmic lesion. The agent which is evaluated can be, e.g., a polysaccharide, a nucleic acid, a fat, polypeptide, or a peptide-mimetic. Amino-acid based agents can share sequence homology with MCH or can be unrelated by sequence homology. E.g., the agent can have 50, 60, 70, 80, 90 or 95% homology with MCH. The agent can be a linear or cyclic peptide.

Accordingly, in another aspect, the invention features a method of evaluating a treatment, e.g., the administration of an agent, for its effect on eating behavior, appetite, or the maintenance of weight. The method includes: administering the treatment to a melanocyte based system, e.g., the one or more of the frog or lizard skin, fish scale, or fish skin assays described herein, and determining if there is a change in the system, and (optionally) administering the treatment to a second test systemand determining the effect of the treatment on a parameter related to eating behavior, appetite, or weight gain or loss in the second system. The second system can be the same or different from the first. In preferred embodiments the second system is a cell-based assy, e.g., an assay which uses: a fish cell; a reptilian cell; an amphibian cell; a mammalian cell; a rodent cell, e.g., a mouse or rat cell; a primate cell; or a human cell. In preferred embodiments: the cell is a neuronal cell, e.g., a GH3 cell, a PC12 cell, or a primary hypothalmic culture cell. In other preferred embodiments the second system is an animal based system, e.g., the treatment is administered to an animal and the effect on a parameter related to eating behavior, e.g., eating behavior itself, is evaluated.

In another aspect, the invention features a method of evaluating a treatment, e.g., the administration of an agent, for its effect on eating behavior, appetite, or the maintenance of weight. The method includes: providing an animal, cell (an animal, plant, or bacterial cell), or cell culture preparation, having a reporter gene linked to the promoter region of MCH; administering the treatment; and determining if there is an effect on reporter gene expression. An effect on reporter gene expression is indicative of an effect on eating behavior, appetite, or the maintenance of weight. In preferred embodiments the cell is: a fish cell; a reptilian cell; an amphibian cell; a mammalian cell; a rodent cell, e.g., a mouse or rat cell; a primate cell; or a human cell. In preferred embodiments the cell is a neuronal cell, e.g., a GH3 cell, a PC12 cell, or a primary hypothalmic culture cell.

In another aspect, the invention features a method of evaluating a treatment, e.g., the administration of an agent, for its effect on eating behavior, appetite, or the maintenance of weight. The method includes: providing an animal, cell (an animal, plant, or bacterial cell), or cell culture preparation, which expresses a receptor which is bound by MCH or which otherwise undergoes a change in its ability to bind a ligand when MCH is applied to the animal or cell, e.g., the MSH receptor, MC3-R; administering the treatment to the animal, cell, or cell culture; and determining (1) if there is a change in a parameter related to binding of a ligand, e.g., an MCH agonist or antagonist, to the receptor or (2) if there is an effect on a parameter related to eating, appetite, or weight loss or gain. In preferred embodiments the cell is a human cell transformed with a heterologus receptor, e.g., the mouse receptor, e.g., a cell from the HEK-293 line or a similar cell. In preferred embodiments the parameter related to ligand/receptor binding includes: a change in a signal transduction-related phenomenon; a change in an interaction, e.g., binding, of a second ligand with the receptor, e.g., a change in the binding of ACTH ligand to the receptor. In other preferred embodiments the cell is: a fish cell; a reptilian cell; an amphibian cell; a mammalian cell; a rodent cell, e.g., a mouse or rat cell; a primate cell; or a human cell. In preferred embodiments the cell is a neuronal cell, e.g., a GH3 cell, a PC12 cell, or a primary hypothalmic culture cell.

In another aspect, the invention features a method of evaluating a treatment, e.g., the administration of an agent, for its effect on eating behavior, appetite, or the maintenance of weight. The method includes: providing a substrate (e.g., a substrate derived from a vertebrate brain, e.g., a brain section or a synaptosome preparation) to which MCH binds; contacting the substrate, MCH, and the agent; and evaluating the ability of the compound to promote or inhibit binding of MCH to the substrate. The ability of the compound to inhibit MCH binding to the substrate can be indicative of MCH agonist or antagonist activity. In preferred embodiments: the agent is other than an antibody; the agent is other than an antibody directed against salmon MCH; the agent is other than a rabbit antibody; the agent is other than a rabbit polyclonal antibody, e.g., other than a rabbit polyclonal anti-fish MCH antibody; the agent is other than a full length antibody, e.g., it is a fragment of an antibody, e.g., a fragment capable of binding MCH.; the MCH polypeptide is in a form other than a crude brain preparation or brain slice; the MCH is substantially free of at least one protein with which it occurs naturally. In other preferred embodiments: the agent is a monoclonal antibody; the agent is is a recombinant or humanized antibody.

In another aspect, the invention features a method of evaluating a treatment, e.g., the administration of an agent, for its effect on eating behavior, appetite, or the maintenance of weight. The method includes: providing a cell, or cell culture preparation; administering the treatment; and determining if there is an effect on MCH RNA or protein levels in the cell, or cell culture preparation. In preferred embodiments the cell is: a fish cell; a reptilian cell; an amphibian cell; a mammalian cell; a rodent cell, e.g., a mouse or rat cell; a primate cell; or a human cell. In preferred embodiments the cell is a neuronal cell, e.g., a GH3 cell, a PC12 cell, or primary hypothalmic culture cell.

In another aspect, the invention features a method of evaluating a treatment, e.g., the administration of an agent, for its effect on eating behavior, appetite, or the maintenance of weight. The method includes: providing a subject animal; administering the treatment; and determining if there is an effect on MCH RNA or protein levels in the animal. The treatment can be any treatment which can result in the desired effect but the administration of agents, e.g., drugs or chemicals, is preferred. Preferably, the treatment is other than surgical intervention, e.g., the production of surgical lesions, e.g., electrolytic lesions, e.g., the treatment is other than a ventromedial hypothalmic lesion, e.g., an electrolytically produced ventromedial hypothalmic lesion.

In preferred embodiments, the animal is a mammal, e.g. a rodent, e.g., a rat or mouse, a dog, or a nonhuman primate. In other embodiments, the animal is other than a rat or mouse.

In preferred embodiments the treatment includes administering an agent and: the agent is other than an antibody; the agent is other than an antibody directed against salmon MCH; the agent is other than a rabbit antibody; the agent is other than a rabbit polyclonal antibody, e.g., other than a rabbit polyclonal anti-fish MCH antibody; the agent is other than a full length antibody, e.g., it is a fragment of an antibody, e.g., a fragment capable of binding MCH; the MCH polypeptide is in a form other than a crude brain preparation or brain slice; the MCH is substantially free of at least one protein with which it occurs naturally. In other preferred embodiments: the agent is a monoclonal antibody; the agent is a recombinant or humanized antibody.

In another aspect, the invention features a method of evaluating an agent, e.g., a polypeptide or peptide-mimetic, for its effect on eating behavior, appetite, or the maintenance of weight. The method includes: administering the agent to an animal, e.g., a mammal, e.g., a rodent, e.g., a rat; and determining if there is an effect on a parameter related to eating behavior. In preferred embodiments, the agent is MCH, or agonist or antagonist thereof. For example, the agonist or antagonist is a peptide analog of MCH having 40, 50, 60, 70, 80, or 90% homology to the native MCH, or it is a polypeptide which binds to MCH or a naturally occurring ligand of MCH, e.g., an MCH receptor, e.g., MC3-R. The agent can be a linear or cyclic polypeptide. In preferred embodiments the compound is other than water and NaCl.

In preferred embodiments: the agent is other than an antibody; the agent is other than an antibody directed against salmon MCH; the agent is other than a rabbit antibody; the agent is other than a rabbit polyclonal antibody, e.g., other than a rabbit polyclonal anti-fish MCH antibody; the agent is other than a full length antibody, e.g., it is a fragment of an antibody, e.g., a fragment capable of binding MCH; the MCH polypeptide is in a form other than a crude brain preparation or brain slice; the MCH is substantially free of at least one protein with which it occurs naturally. In other preferred embodiments: the agent is a monoclonal antibody; the agent is a recombinant or humanized antibody. In another aspect, the invention features, a method of evaluating an agent for the ability to bind an MCH polypeptide. The method includes: contacting the agent with the MCH polypeptide, or a purified preparation thereof, and evaluating ability of the compound to form a complex with the MCH polypeptide. This method can be performed in vitro, or in vivo, e.g., in a two-hybrid interaction trap assay. In preferred embodiments; the agent is other than an antibody directed against salmon MCH; the agent is other than a rabbit antibody; the agent is other than a rabbit polyclonal antibody, e.g., other than a rabbit polyclonal anti-fish MCH antibody; the agent is other than a full length antibody, e.g., it is a fragment of an antibody, e.g., a fragment capable of binding MCH; the MCH polypeptide is in a form other than a crude brain preparation or brain slice; the MCH is substantially free of at least one protein with which it occurs naturally. In other preferred embodiments: the agent is a monoclonal antibody; the agent is a recombinant or humanized antibody.

In another aspect, the invention features, a method of evaluating an agent, e.g., a fragment of an MCH peptide, for the ability to bind, or to alter, a naturally occurring ligand of MCH, e.g., an MCH receptor, e.g., MC3-R. Alter includes, e.g., sterically altering the receptor, or altering the binding properties of the receptor for an MCH polypeptide or for another ligand. The method includes: contacting the agent with the MCH ligand; and evaluating the ability of the agent to form a complex with the MCH ligand, e.g., the ability of the agent to inhibit MCH peptide/MCH ligand interaction, or to alter the receptor. This method can be performed in vitro, or in vivo, e.g., in a two-hybrid interaction trap assay. In preferred embodiments: the receptor is other than mouse MC3-R; the agent is a peptide analog of MCH having 40, 50, 60, 70, 80, 90% or more homology with MCH; the agent is a linear or cyclic polypeptide.

In yet another aspect, the invention features a method for evaluating an agent, e.g., for the ability to modulate an interaction of an MCH peptide with a second polypeptide, e.g., a naturally occurring ligand of MCH, e.g., an MCH receptor, e.g., MC3-R. The method includes the steps of (i) combining a second polypeptide (or preferably a purified preparation thereof), an MCH polypeptide (or preferably a purified preparation thereof), and the agent, e.g., under conditions wherein in the absence of the agent, the second polypeptide, and the MCH polypeptide are able to interact, e.g., to form a complex; and (ii) detecting the interaction, e.g., detecting the formation (or dissolution) of a complex which includes the second polypeptide, and the MCH peptide. A change, e.g., a decrease or increase, in the formation of the complex in the presence of the agent (relative to what is seen in the absence of the agent) is indicative of a modulation, e.g., an inhibition or promotion, of the interaction between the second polypeptide, and the MCH peptide. In preferred embodiments: the second polypeptide, and the MCH peptide, are combined in a cell-free system and contacted with the agent; the cell-free system is selected from a group consisting of a cell lysate and a reconstituted protein mixture; the MCH peptide and the second polypeptide are simultaneously expressed in a cell, and the cell is contacted with the agent, e.g., the method includes an interaction trap assay (e.g., a two-hybrid assay). In preferred embodiments: the receptor is other than mouse MC3-R; the agent is a peptide analog of MCH having 40, 50, 60, 70, 80, 90% or more homology with MCH; the agent is a linear or cyclic polypeptide.

In preferred embodiments; the agent is other than an antibody directed against salmon MCH; the agent is other than a rabbit antibody; the agent is other than a rabbit polyclonal antibody, e.g., other than a rabbit polyclonal anti-fish MCH antibody; the agent is other than a full length antibody, e.g., it is a fragment of an antibody, e.g., a fragment capable of binding MCH; the MCH polypeptide is in a form other than a crude brain preparation or brain slice; the MCH is substantially free of at least one protein with which it occurs naturally. In other preferred embodiments: the agent is a monoclonal antibody; the agent is a recombinant or humanized antibody.

In yet another aspect, the invention features a two-phase method (e.g., a method having an in vitro and an in vivo phase) for evaluating an agent, e.g., for the ability to modulate, e.g., to inhibit or promote, an interaction of an MCH peptide with a naturally occurring ligand of MCH, e.g., an MCH receptor, e.g., MC3-R. The method includes steps (i) and (ii) of the method described immediately above performed in vitro, and further includes: (iii) determining if the agent modulates the interaction in vitro and if so; (iv) administering the agent to a cell or animal; and (v) evaluating the in vivo effect of the agent on an interaction, e.g., inhibition, of an MCH peptide with a second polypeptide, e.g., by the effect on eating behavior.

In another aspect, the invention features a two-phase method (e.g., a method having a primary in vitro and a secondary in vivo phase) for evaluating a treatment. The method can be used to evaluate a treatment for the ability to modulate, e.g., to inhibit or promote, an MCH-mediated phenomenon, e.g., an aspect of feeding behavior, appetite, or the maintenance of weight, or to evaluate a test agent for use as a therapeutic agent. The method includes: (i) an in vitro phase in which the test agent is contacted with a cell, or a cell free system, which includes a reporter gene functionally linked to an MCH regulatory sequence, and detecting the modulation of the expression of the reporter gene and (ii) if the test agent modulates the expression, administering the test compound to an animal, and evaluating the in vivo effects of the compound on an aspect of feeding behavior, e.g., the level of MCH expression.

In another aspect, the invention features, a method of evaluating an agent for the ability to bind a nucleic acid encoding an MCH regulatory sequence. The method includes: contacting the agent with the nucleic acid; and evaluating ability of the compound to form a complex with the nucleic acid.

In another aspect, the invention features a method of evaluating an effect of a treatment, e.g., a treatment for treating a disorder characterized by unwanted eating behavior, or a condition of under or overweight. The method uses a test cell or organism which misexpresses an MCH gene. The method includes: administering the treatment to a test cell or organism, e.g., a cultured cell, or a mammal, and evaluating the effect of the treatment on an aspect of MCH metabolism. An effect on an aspect of MCH metabolism indicates an effect of the treatment. In preferred embodiments: the effect on an aspect of MCH metabolism is a change in eating behavior or weight, a change in MCH mRNA levels, a change in MCH protein levels.

In preferred embodiments the cell is: a fish cell; a reptilian cell; an amphibian cell; a mammalian cell; a rodent cell, e.g., a mouse or rat cell; a primate cell; or a human cell. In preferred embodiments the cell is a neuronal cell, e.g., a GH3 cell, a PC12 cell, or primary hypothalmic culture cell.

In preferred embodiments the treatment is the administration of an agent and: the agent is other than an antibody directed against salmon MCH; the agent is other than a rabbit antibody; the agent is other than a rabbit polyclonal antibody, e.g., other than a rabbit polyclonal anti-fish MCH antibody; the agent is other than a full length antibody, e.g., it is a fragment of an antibody, e.g., a fragment capable of binding MCH; the MCH polypeptide is in a form other than a crude brain preparation or brain slice; the MCH is substantially free of at least one protein with which it occurs naturally. In other preferred embodiments: the agent is a monoclonal antibody; the agent is a recombinant or humanized antibody.

In another aspect, the invention features a method of evaluating an effect of a treatment, e.g., a treatment for treating a disorder characterized by unwanted eating behavior, or a condition of under or overweight. The method uses a test cell or organism which includes MCH transgene. The method includes: administering the treatment to a test cell or organism, e.g., a cultured cell, or a mammal, and evaluating the effect of the treatment on an aspect of MCH metabolism. An effect on an aspect of MCH metabolism indicates an effect of the treatment. In preferred embodiments: the effect on an aspect of MCH metabolism is a change in eating behavior or weight, a change in MCH mRNA levels, a change in MCH protein levels. The test cell or organism can be wild type or mutant at one or more loci other than MCH, e.g., ob, or ob receptor. The subject can also be deficient for brown fat tissue. E.g., a brown fat tissue "knockout" mouse can be made by fusing diphtheria toxin to a brown fat-specific promoter.

In preferred embodiments the cell is: a fish cell; a reptilian cell; an amphibian cell; a mammalian cell; a rodent cell, e.g., a mouse or rat cell; a primate cell; or a human cell. In preferred embodiments the cell is a neuronal cell, e.g., a GH3 cell, a PC12 cell, or primary hypothalmic culture cell.

In preferred embodiments the treatment is the administration of an agent and: the agent is other than an antibody directed against salmon MCH; the agent is other than a rabbit antibody; the agent is other than a rabbit polyclonal antibody, e.g., other than a rabbit polyclonal anti-fish MCH antibody; the agent is other than a full length antibody, e.g., it is a fragment of an antibody, e.g., a fragment capable of binding MCH; the MCH polypeptide is in a form other than a crude brain preparation or brain slice; the MCH is substantially free of at least one protein with which it occurs naturally. In other preferred embodiments: the agent is a monoclonal antibody; the agent is a recombinant or humanized antibody.

In another aspect, the invention features a method of evaluating an effect of a treatment, e.g., a treatment for treating a disorder characterized by unwanted eating behavior, or a condition of under or overweight. The method uses a test cell or organism which expresses a wild-type MCH gene. The method includes: administering the treatment to a test cell or organism, e.g., a cultured cell, or a mammal, and evaluating the effect of the treatment on an aspect of MCH metabolism. An effect on an aspect of MCH metabolism indicates an effect of the treatment. In preferred embodiments: the effect on an aspect of MCH metabolism is a change in eating behavior or weight, a change in MCH mRNA levels, a change in MCH protein levels. The test cell or organism can be wild type or mutant at one or more loci other than MCH, e.g., ob, or ob receptor. The subject can also be deficient for brown fat tissue. E.g., a brown fat tissue "knockout" mouse can be made by fusing diphtheria toxin to a brown fat-specific promoter.

In preferred embodiments the cell is: a fish cell; a reptilian cell; an amphibian cell; a mammalian cell; a rodent cell, e.g., a mouse or rat cell; a primate cell; or a human cell. In preferred embodiments the cell is a neuronal cell, e.g., a GH3 cell, a PC12 cell, or primary hypothalmic culture cell.

In preferred embodiments the treatment is the administration of an agent and: the agent is other than an antibody directed against salmon MCH; the agent is other than a rabbit antibody; the agent is other than a rabbit polyclonal antibody, e.g., other than a rabbit polyclonal anti-fish MCH antibody; the agent is other than a full length antibody, e.g., it is a fragment of an antibody, e.g., a fragment capable of binding MCH; the MCH polypeptide is in a form other than a crude brain preparation or brain slice; the MCH is substantially free of at least one protein with which it occurs naturally. In other preferred embodiments: the agent is a monoclonal antibody; the agent is a recombinant or humanized antibody.

In another aspect, the invention provides, a method of determining if a subject mammal, e.g., a primate, e.g., a human, is at risk for an MCH related disorder, a weight-related disorder, or an eating or appetite disorder. In preferred embodiments the method is used to evaluate whether the subject is at risk for a genetically conditioned disorder. Eating disorders include, e.g., a disorder characterized by unwanted eating behavior. The method includes detecting, in a tissue of the subject, the presence or absence of a mutation of an MCH gene. In preferred embodiments: detecting the mutation includes ascertaining the existence of at least one of: a deletion of one or more nucleotides from the MCH gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from MCH gene or naturally occurring mutants thereof or 5' or 3' flanking sequences naturally associated with the MCH gene; (ii) exposing the probe/primer to nucleic acid of the tissue; and (iii) detecting, by hybridization of the probe/primer to the nucleic acid, the presence or absence of the genetic lesion.

Circulating white cells can be used as source of genomic DNA in the diagnostic methods described herein. Prior art methods, e.g., the single strand conformation polymorphism (SSCP) method, can be used to detect lesions or polymorphisms. The diagnostic methods used herein can be used to screen overweight subjects, e.g., obese, or morbidly obese subjects, for MCH gene lesions or polymorphisms.

In preferred embodiments the method further includes determining if the subject is overweight, obese, or morbidly obese. In preferred embodiments the subject is overwieght, obese, or morbidly obese.

In another aspect, the invention provides, a method of determining if a subject mammal, e.g., a primate, e.g., a human, is at risk for an MCH related disorder, a weight related disorder, or an eating disorder. In preferred embodiments the method is used to evaluate whether the subject is at risk for a genetically conditioned disorder. The method includes detecting, in a tissue of the subject, the non wild type levels of MCH RNA or protein. In preferred embodiments the method further includes determining if the subject is overweight, obese, or morbidly obese. In preferred embodiments the subject is overwieght, obese, or morbidly obese.

In another aspect, the invention provides, a method of determining if a subject mammal, e.g., a primate, e.g., a human, is at risk for an MCH related disorder, a weight related disorder, or an eating disorder. In preferred embodiments the method is used to evaluate whether the subject is at risk for a genetically conditioned disorder The method includes detecting, in a tissue of the subject, the misexpression of a gene encoding an MCH peptide. In preferred embodiments: detecting the misexpression includes ascertaining the existence of at least one of: an alteration in the level of a messenger RNA transcript of the gene; the presence of a non-wild type splicing pattern of a messenger RNA transcript of the gene; or a non-wild type level of the protein. In preferred embodiments the method further includes determining if the subject is overweight, obese, or morbidly obese. In preferred embodiments the subject is overweight, obese, or morbidly obese.

In another aspect, the invention features a method of making an MCH polypeptide, e.g., a MCH polypeptide having a non-wild type activity, e.g., an antagonist, agonist or super agonist of a naturally occurring MCH. The method includes: altering the sequence or ring structure of an MCH peptide, preferably a mammalian, e.g., a human or rat peptide, or a peptide other than a fish, amphibian or reptilian peptide, and testing the altered peptide for the desired activity, e.g., by administering it to an animal and determining its effect on MCH RNA or protein levels, eating behavior or weight.

In another aspect, the invention features a cell or purified preparation of cells which include a MCH transgene or which misexpress the MCH gene. The cell preparation can consist of human or non human cells, e.g., rodent cells, e.g., mouse or rat cells, rabbit cells, or pig cells. In preferred embodiments, the cell or cells include a MCH transgene, e.g., a heterologous form of the MCH gene, e.g. a gene derived from humans (in the case of a non-human cell). In other preferred embodiments, the cell or cells include a gene which misexpress an MCH gene, e.g., an endogenous MCH gene. In preferred embodiments, MCH is over or under expressed. Such cells can serve as a model for studying disorders which are related to mutated or mis-expressed MCH alleles or for use in drug screening.

In another aspect, invention features, a transgenic MCH non-human animal, e.g., a rodent, e.g., a mouse or a rat, a rabbit, or a pig. In preferred embodiments, the transgenic animal includes (and preferably express) a heterologous form of the MCH gene, e.g., a gene derived from humans. In other preferred embodiments, the animal has an MCH gene, e.g., an endogenous MCH gene which is misexpressed, e.g., a knockout or an overexpressed MCH gene. Such a transgenic animal can serve as a model for studying disorders which are related to mutated or mis-expressed MCH alleles or for use in drug screening.

For example, the invention includes a method of evaluating the effect of the expression or misexpression of a MCH gene on a parameter related to eating behavior. The method includes: providing a transgenic animal having a MCH transgene; contacting the animal with an agent, e.g., an analog of MCH; and evaluating the effect of the transgene on the parameter (e.g., by comparing the value of the parameter for a transgenic animal with the value for a control, e.g., a wild type animal).

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning A Laboratory Manual,* 2nd Ed., ed. by Sambrook, Fritsch and Maniatis (Cold Spring Harbor Laboratory Press: 1989); *DNA Cloning,* Volumes I and II (D. N. Glover ed., 1985); *Oligonucleotide Synthesis* (M. J. Gait ed., 1984); Mullis et al. U.S. Pat. No: 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I–IV (D. M. Weir and C. C. Blackwell, eds., 1986); *Manipulating the Mouse Embryo,* (Cold Spring Harbor Laboratory Press, Cold Spring Harbor, N.Y., 1986).

Other features and advantages of the invention will be apparent from the following detailed description, and from the claims.

DETAILED DESCRIPTION OF THE INVENTION

The drawings are briefly described.

DEFINITIONS

Figure 1:
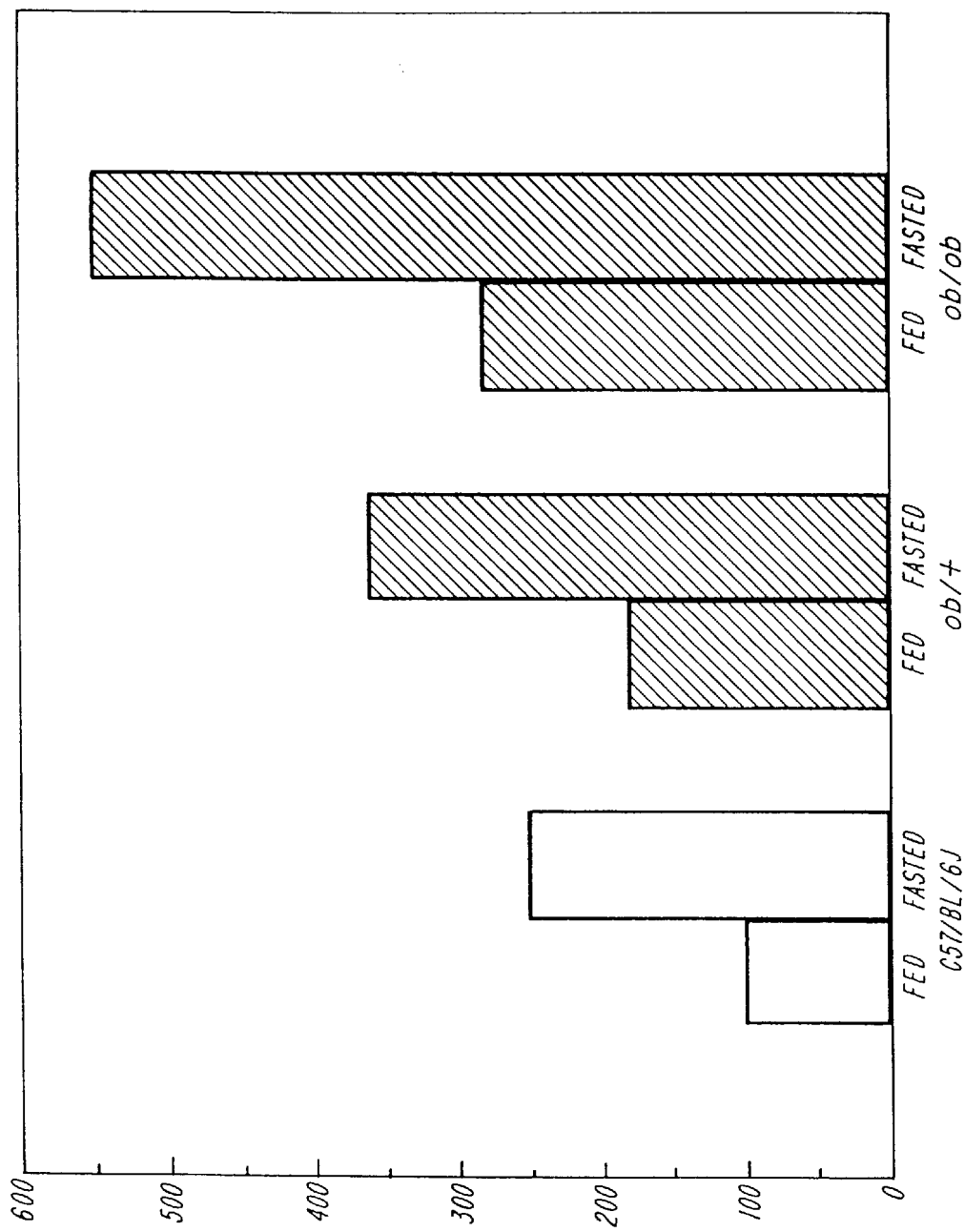
FIG. 1 is a bar graph depicting MCH levels in fed versus fasted mice (after 24 hr of fasting) of the following genotype: C57/BL/6J (wild type), ob/+, and ob/ob.

MCH antagonist, as used herein, refers to agents which result in an inhibition of feeding behavior. Antagonists include agents with significant amino acid homology to MCH as well as agents which are unrelated by amino acid sequence homology or which are not polypeptides. Antagonists include agents which act by competitively or non-competitively binding an MCH receptor but can also include agents which act downstream from the receptor, e.g., in intacellular signaling, or independent of the MCH receptor. Antagonist includes "action" antagonists, e.g., agents which act by a partly or entirely different pathway to affect eating behavior.

Misexpression, as used herein, refers to a non-wild type pattern of gene expression. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

A substantially pure nucleic acid, e.g., a substantially pure DNA, is a nucleic acid which is one or both of: not immediately contiguous with both of the coding sequences with which it is immediately contiguous (i.e., one at the 5' end and one at the 3' end) in the naturally-occurring genome of the organism from which the nucleic acid is derived; or which is substantially free of a nucleic acid sequence with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other DNA sequences. Substantially pure DNA also includes a recombinant DNA which is part of a hybrid gene encoding additional MCH sequence.

A purified preparation or a substantially pure preparation of a polypeptide, as used herein, means a polypeptide that has been separated from other proteins, lipids, and nucleic acids with which it naturally occurs. Preferably, the polypeptide is also separated from substances, e.g., antibodies or gel matrix, e.g., polyacrylamide, which are used to purify it. Preferably, the polypeptide constitutes at least 10, 20, 50 70, 80 or 95% dry weight of the purified preparation. Preferably, the preparation contains: sufficient polypeptide to allow protein sequencing; at least 1, 10, or 100 μg of the polypeptide; at least 1, 10, or 100 mg of the polypeptide.

PREPARATION OF PEPTIDE ANALOGS OF MCH

Synthetic MCH and its analogs can be prepared to identify agonists and antagonists, and determine the structural requirements for MCH agonist or antagonist activity. MCH can be modified in a number of ways, e.g., by shortening either (or both) the amino- or carboxy-terminal regions, contracting the cysteine bridged ring, forming acyclic analogs, or modifying or substituting an amino acid, e.g., a residue, within, or outside, the ring. Synthetic MCH and its analogs can be assayed using one or more of the assays described herein.

Generally, the synthetic schemes use the Merrifield solid phase synthesis followed by cyclization and purification as described, e.g., in Lebl et al. (1988) *J. Med. Chem.* 31:949–954, herein incorporated by reference. Briefly, chloromethylated resin can be used as the support to introduce the first amino acid on an automated synthesizer, e.g. a DuPont 2200. The intact peptides are cleaved from the resin and then washed. Following extraction from the wash the peptides are lyophilized. The lyophilized protein is dissolved in degassed water. Cyclization is achieved by the dropwise addition of potassium ferricyanide ($K_3Fe(CN)_6$). Purification can be performed by column chromatography on Sephadex G-25, carboxymethyl cellulose and by reversed-phase high-performance chromatography (HPLC).

Alternatively, truncated MCH analogs can be prepared by exposing natural or synthetic MCH to enzymes. Natural MCH can be isolated from pituitaries using an acetone extraction and purified on an HPLC column as described in Kawauchi et al. (1988) *Adv. in Pigment Cell Res.* 517–530, herein incorporated by reference. For example, $MCH_{1-14}$, a carboxy-terminal truncation, can be generated from MCH by exposure to carboxypeptidase Y.

Acyclic analogs can be constructed by replacing the $Cys^5$–$Cys^{14}$ bridge with pseudoisosteric residues. Either L-serine, a polar substitute, or L-α-aminobutyrate, a nonpolar substitute, can be utilized. The peptides, with the appropriate substitution, can be prepared by solid phase synthesis as described above and in Matsunaga et al., *Life Sci.* (1992) 51:679–685, herein incorporated by reference.

Modification of amino acids within the ring is performed with a reagent specific to each residue. Modifications can be accomplished either by substituting a different amino acid or altering the existing amino acid. For example, the Tyr residue at position 11 can be modified with the addition of a —$NO_2$ group by exposing MCH to a solution of 10% nitromethane-95% ethanol. See, e.g., Kawauchi et al. (1988) *Adv. in Pigment Cell Res.* 517–530, herein incorporated by reference.

ASSAYS FOR MCH AGONIST AND ANTAGONIST ACTIVITY

Frog/Lizard Melanocyte Assay

The activity of compounds, e.g., MCH and related analogs, e.g., MCH agonists or antagonists, can be determined by in vitro assay using skins from frogs (*R. pipiens*) and lizards (*A. carolinensis*) (e.g., see Castrucci et al. (1989) *Gen. Comp. Endocrinol.* 73:157–163, and Hruby et al. (1987) *J. Med. Chem.* 30:2126–2130, herein incorporated by reference). These assays are based upon the amount of light reflected from the surface of the skins in vitro. In these assays, melanin granules (melanosomes) within melanocytes migrate outward into the dendritic processes of the pigment cells in response to MCH. This centrifugal granule translocation results in darkening of the skins. The changes in reflectance are measured by a reflectometer and are usually expressed as a percent change from the initial base (zero time) values. An increase in reflectance indicates skin lightening whereas a decrease in reflectance indicates skin darkening. Removal of the MCH (i.e., by rinsing with Ringer solution) from the incubation medium usually results in a perinuclear aggregation of melanosomes leading to a lightening of the skins back to original base values.

Briefly, frogs or lizards are sacrificed by decapitation and the leg and thigh skins are removed and kept viable in a bath of physiological saline (Ringer) solution. Skins can than be stretched over PVC rings and the baseline light reflectance measured by reflectometer. For example, to assay for antagonistic activity, the skins can be pre-incubated for 1 hour in various concentrations of the potential antagonist. After this period, a known concentration of MCH can be added and its activity determined in the same assay. Therefore, dose response curves for each potential MCH agonist or antagonist and the relative potency, as compared to MCH, can be calculated.

Fish Scale Melanocyte Assay

The activity of compounds, e.g., MCH and related analogs, e.g., agonists or antagonists, can also be evaluated in various fish scale-based melanocyte assays. In this assay fish scales are used to visualize the actions of MCH related compounds. The scales from a variety of fishes, such as the yearling tilapia (*Oreochromis mossambicus*), can be used. See, e.g., Hogben and Slome (1931) *Proc. R. Soc.* B108:10–53, herein incorporated by reference.

Briefly, the scales are incubated in a solution that disperses the melanin causing the scales to darken. A sample of unknown MCH activity is added. If there is MCH-like activity the melanin is concentrated causing the scales to lighten. Alternatively, the scales can be incubated with a combination of MCH and putative antagonist to evaluate the antagonists potency. The scales are evaluated visually under a microscope. See, e.g., Kawauchi et al., *Nature*, 305:321–323 (1983), incorporated herein by reference.

Teleost Skin Melonocyte Bioassays

Yet another method utilizes the teleost fish, *Synbranchus marmoratus*, to evaluate the melanosome aggregating activity of MCH, MCH analogs, or a sample containing unknown MCH activity. In this assay the "resting" (unstimulated) state of the melanophores is characterized by dispersed melanosomes, i.e., the skin is darkened. Therefore, the assay is particularly appropriate for the study of melanosome aggregating agents such as MCH. This assay can be performed as essentially disclosed in Casstucci et al., *Gen. Comp. Endocrin.*, 66:374–380 (1987), incorporated herein by reference.

Briefly, fish skins are cut into pieces approximately 2.5× 2.5 cm, placed between two rings (either PVC or metal), and allowed to equilibrate in a suitable buffered solution, preferably Tyrode's or Ringer's, for an hour. In the resting (unstimulated) state the skins are darkened. MCH is added to the bath and incubated with the fish skins for 60 minutes. The changes in skin color are measured by a reflectometer. The MCH will cause the skins to lighten and will result in higher reflectance values.

In vivo melanocyte bioassay

The MCH-like activity of analogs or samples can also be evaluated in an intact organism. If rainbow trout are exposed to a black background their scales will darken. Intraperitoneal injections of MCH, its analog, or a sample of unknown MCH activity into the darken trout will result in a lightening of the scales if there is MCH-like activity. The effect is rapid in onset and lasts for several hours if there is MCH-like activity. This assay can be performed as essentially disclosed in Kawauchi et al., *Adv. Pigment Cell Res.*, 517–530 (1988), incorporated herein by reference.

Radioimmunoassay and Immunohistochemistry: Methods for Detecting the Levels of MCH Binding to a Substrate The concentration of MCH in an individual or a tissue sample can be determined by radioimmunoassay. The sample containing an unknown MCH concentration is compared with a standard of known concentration. As a sample contains an increasing amount of MCH there will be more unlabeled MCH available for binding to the anti-MCH antibody relative to radiolabeled MCH resulting in less radiolabeled MCH being bound by the anti-MCH antibody. This can be used to determine the binding of MCH or an analog thereof to a substrate in, e.g., the presence or absence of another compound, e.g., a putative antagonist. Generally, a sample is obtained from the subject and protein samples prepared. Rabbit anti-MCH can serve as the primary antibody and is incubated with the protein sample to which a radiolabeled MCH had been added. Goat anti-rabbit is then added to aid in precipitating the MCH-rabbit antibody complex. Following an incubation period the sample is centrifuged and the resulting pellet is counted. The more MCH there is in the sample the less radioactivity will be found in the resulting pellet. This assay can be performed as essentially disclosed in Zamir et al., supra.

Localization of MCH can be accomplished by fluorescent immunohistochemistry. For example, rat brains can be sectioned into 20 $\mu$M thick slices and placed onto microscope slides. The slices are incubated with a rabbit anti-MCH antibody or equivalent antibody. The slices are washed to remove excess antibody. An incubation with a fluorescently labeled goat anti-rabbit antibody allows for localization of the MCH-like material. Fluorescence can be monitored with a fluorescence microscope. This assay can be performed as essentially disclosed in Zamir et al., *Proc. Natl. Acad. Sci. USA,* 83:1528–1531 (1986), herein incorporated by reference.

Synaptosome Binding

The ability of a compound to bind a naturally occurring MCH receptor, e.g., the ability of analogs to competitively antagonize MCH, can be determined utilizing radiolabeled MCH in binding assays. A competitive antagonist can prevent MCH from interacting with its receptor and less radioactivity would be bound. A highly tritiated-MCH has been synthesized and is available for whole cell binding studies, see, e.g., Drozdz and Eberle, *J. Receptor & Signal Transduction Res.* 15(1–4):487–502 (1995), herein incorporated by reference. Methods for iodinating MCH have also been developed, see, e.g., Drozdz and Eberle, *23rd European Peptide Symposium,* Braga, Portugal (1994), hereby incorporated by reference.

Generally, the tissue sample of interest is homogenized when preparing membranes or synaptosomes, or digested with enzymes for whole cells. Whole cells, membranes or synaptosomes can then be isolated by centrifugation. For example, membranes can be prepared by homogenizing the tissue sample, and centrifuging the resultant solution. The supernatant is collected and centrifuged. The pellet is resuspended and passed through a small gauge needle. The crude membrane pellet is resuspended in an appropriate binding buffer. Membranes are exposed to a constant concentration of radiolabeled MCH and varying concentrations of the analog of interest. Unbound $^3$H-MCH is separated from the bound $^3$H-MCH by a rapid filtration over fiber glass filters. The filters are washed and counted. See, e.g., Drozdz and Eberle, *J. Receptor & Signal Transduction Res.* 15(1–4):487–502 (1995), herein incorporated by reference.

HEK-293 Assay

As discussed herein, heterologous human kidney, HEK-293 cells stably transfected with a plasmid carrying MC3-R can be used to assay MCH activity. It is not clear whether the MCH interaction with the MC3-R receptor is direct or indirect, but application of MCH results in an increase in binding of ACTH to the MC3-R receptor. Scatchered analysis suggests an increase in ACTH binding sites, so the effect of MCH may be to induce a steric change in the receptor. Exposure of cells to 10–7M MCH for 20 minutes or overnight results in a 15–100% increase in ACTH binding.

In vivo Rodent Brain Assay

As discussed herein, rodents, e.g., rats, can be used to assay MCH activity in vivo. A Teflon catheter can be inserted into the third ventricle of a rat and cemented into place. MCH or its analogs, e.g., agonists or antagonists, can be introduced by way of the catheter at various concentrations, and their effect on eating behavior determined.

IDENTIFICATION OF GENES PREFERENTIALLY EXPRESSED IN OB/OB HYPOTHALAMUS BY PCR DISPLAY

PCR display was used to identify differential expression of neuropeptides that might be important in appetite regulation in the hypothalamus of obese rodents. PCR display allows screening for differential gene expression with relatively small amounts (100 $\mu$g) of mRNA (Lian and Pardee, 1992, *Science* 257:967–971).

PCR display was performed as follows. Male C57b16J ob/ob, ob/+ heterozygotes, and unaffected C57b16J mice were obtained at 7 weeks of age from Jackson Laboratories (Bar Harbor, Me.). Mice were housed for at least 4 days after arrival, to allow them to recover from shipping. Fed mice were sacrificed in the morning, after being anesthetized with an IP injection of 200 mg/kg of sodium amytal. In small experiments food was withdrawn at the time interval described. Mice were decapitated, the brains were removed, and the hypothalami identified, excised, and extracted immediately in RNAzol (Cinna/Biotex Laboratories, Houston, Tex.). 10 hypothalami, weighing approximately 100 mg, were collected and then homogenized using a hand held homogenizer.

Aliquots of total RNA were treated with DNAase I (Boehringer Mannheim, Indianapolis, Ind.) to remove any traces of DNA. RNA was divided into nine pools, and a cDNA was synthesized using MMTV reverse transcriptase (Superscript RNAaseH, Gibco BRL, Gaithersburg, Md.), and one of nine anchored primers (see below). cDNA, thus generated, was used in PCR display.

12 possible downstream primers with the sequence $T_{12}XY$ (where X and Y are any nucleotide) and termed anchored primers, were used in conjunction with approximately 50 upstream random primers, designated arbitrary primers for PCR display. The arbitrary upstream primers did not contain more than 50% GC and had no internal homology to each other. Using these 600 primer pairs, it was possible to assess expression of about 30,000 mRNAs (each primer pair yielded approximately 50 cDNA bands). In the present study, 180 primers pairs consisting of one of nine anchored primers and 20 arbitrary primers were used to screen mRNA expression in hypothalamus of obese vs. non-obese animals. cDNA generated from the reverse transcriptase reaction was amplified using Amplitaq DNA polymerase (Perkin Elmer, Norwalk Conn.). Reactions were performed in the presence of $^{35}$S-ATP (NEN, Boston, Mass.), and products were separated on sequencing gels. Dried gels were exposed to Kodak X-OMAT AR film (Eastman Kodak, Rochester, N.Y.) for 24 to 48 hours. After development, DNA fragments from ob/ob and ob/+ hypothalamus were compared.

ANALYSIS OF OB/OB EXPRESSED GENES

52 DNA bands appeared to be differentially expressed on the PCR display reaction. 35 of these 52 bands were evaluated using Northern blot analysis with riboprobes. Of these no signal could be detected for 9 bands, and no difference in expression was observed in 20 bands. Thus, of about 9,000 cDNAs screened, differences in expression were confirmed for only six bands (or about 0.7%). Of these, two had matches in Gene Bank: one was melanin concentrating hormone (MCH) and the other, the mouse oncogene, fau. A third band had homology to a DNA binding factor, and three additional bands which were differentially expressed had no known homology. Although the difference in MCH expression on differential display appeared to be absolute, i.e. no signal was detected in the ob/+ mice versus an obvious signal in ob/ob mice, assessment of MCH expression using a ribonuclease protection assay showed that the difference between fed ob/ob and ob/+ mice was a rather modest 50–80% increase in the ob/ob animals.

Differentially expressed bands were identified as follows. Bands unique to either ob/ob or ob/+ hypothalamus were excised from the dried gel and were extracted by boiling 100 $\mu$L of TE buffer and precipitated with ethanol in the presence of muscle glycogen (Boehringer Mannheim, Indianapolis, Ind.). DNA was further amplified using the original set of primers used to generate the particular band, under the same thermal cycling conditions. Reaction products were run out on a 1% agarose gel and stained with ethidium bromide. Bands were excised from the gel, eluted, and ligated into the pCR plasmid (InVitrogen, San Diego, Calif.).

Bands inserted into the pCR vector were sequenced using dideoxysequencing in order to determine both sequence and orientation. Depending on orientation, the T4 or T7 promoter was utilized to generate a riboprobe. Riboprobes were used to probe Northern blots containing 20 $\mu$g/lane of RNA from ob/ob or ob/+ hypothalamus. Northern blots were exposed to either Kodak X-OMAT film or analyzed using the Molecular Dynamics PhosphoImager.

EXPRESSION OF MCH

To further evaluate the difference in expression of MCH in lean versus obese mice, and to evaluate the possibility that differences were susceptible to nutritional status, control C57B16J mice, C57B16J ob/+ heterozygotes and C57B16J ob/ob animals were compared both in the fed state and after 24 hours of fasting. FIG. 1 shows quantitative data derived from hypothalmic mRNA blots in fed and fasted mice probed with MCH. MCH expression is 233% increased in fed ob/ob mice when compared to lean mice without the ob gene. Lean heterozygotes are intermediate between the two mice and MCH mRNA is 156% increased over control levels. Fasting for 24 hours increased MCH expression in all three groups of mice. Expression in control mice was increased to 233% compared to fasted animals. The relative ratio of MCH mRNA levels in control, ob/+ and ob/ob mice remained the same, but the total of MCH mRNA doubled for each group.

Levels of NPY mRNA were measured as "control" neuropeptide. In the fed state NPY expression was slightly higher (161%) in ob/ob mice as compared to either control homozygote or ob/+ mice. Levels of NPY mRNA rose with fasting and NPY expression (control fasted 172% of fed mice) was two fold higher in fasted ob/ob mice as compared to fed ob/ob.

The changes in MCH expression over time were also evaluated in fasted C57B16J lean animals. A rise in MCH expression was detected six hours after onset of fasting and increased through 24 hours.

Because, other investigators have reported extra-hypothalamic expression, Northern blots loaded with 30 $\mu$g of RNA and probed with a riboprobe were used to screened a panel of organs for MCH expression. No MCH signal could be detected except in the hypothalamus.

ADMINISTRATION OF MCH IN VIVO

Figure 2:
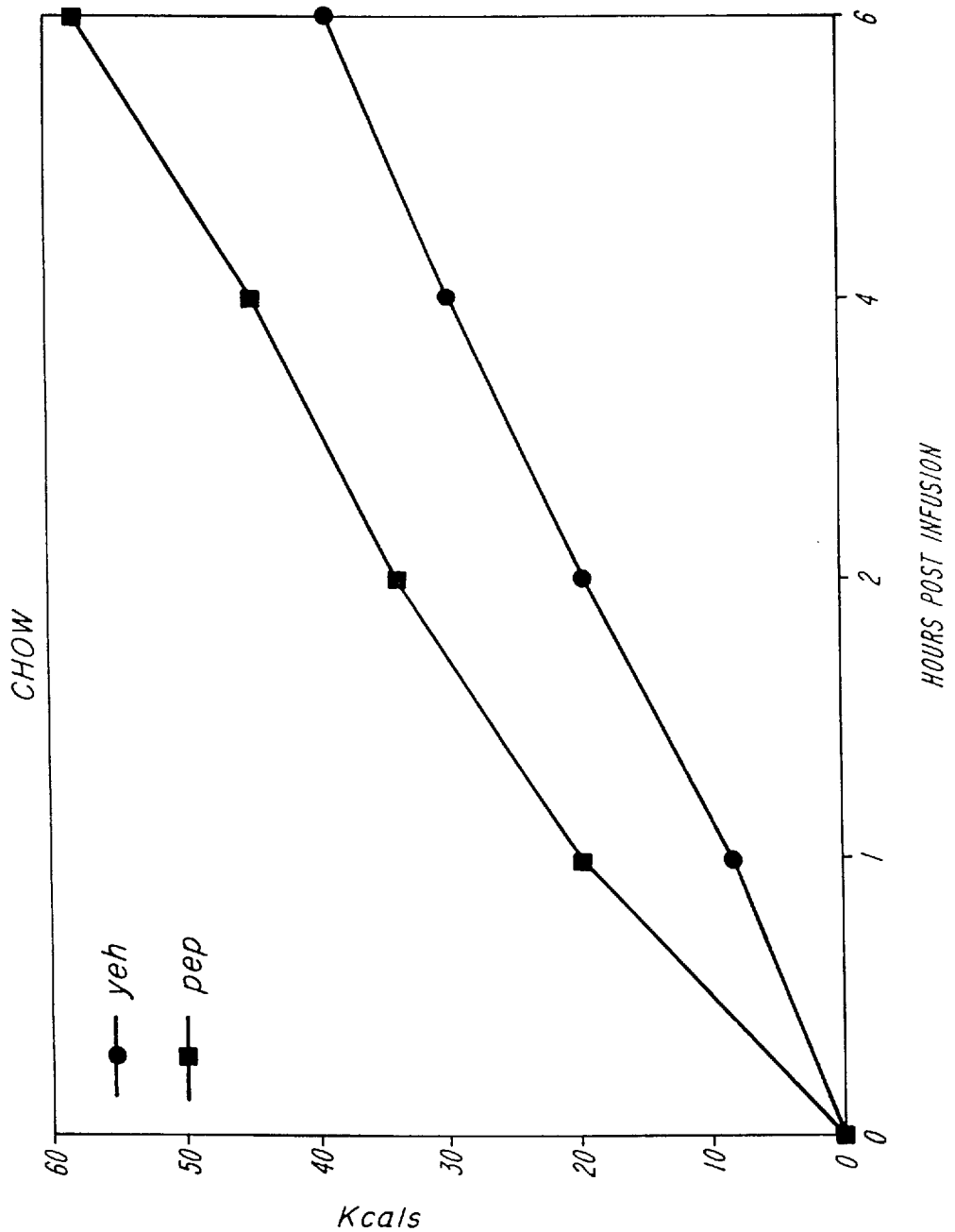
FIG. 2 is a graph depicting doubling of Kcal consumed within 1 hour in rats injected intraventricularly with 5 μg of MCH.

To further evaluate the importance of MCH as an appetite regulator, a Teflon catheter was inserted into the third ventricle of a rat and cemented into place, followed by intraventricular injection of 5 $\mu$g of MCH in 5 $\mu$l of phosphate buffered saline. Control animals received only phosphate buffered saline. Administration of MCH increased feeding behavior, more than doubling Kcal consumed within one hour (FIG. 2).

STRUCTURAL REQUIREMENTS FOR MCH ACTIVITY

A significant amount of work has been done on determining structural requirements for MCH-like activity in melanocyte assay systems using analogs of salmon MCH peptide. Analogs derived from this work can be tested for MCH-like activity using methods of the invention, e.g., in vivo rat assay or in vitro HEK-293 receptor binding assay, or new MCH analogs, e.g., human MCH analogs, based on the prior art knowledge on structural requirements, can be synthesized and tested for activity in one of the in vivo or in vitro assays described herein.

Numerous investigators have synthesized N-terminal and C-terminal fragment analogs of salmon MCH and have tested them for MCH activity in teleost skin bioassay and frog and lizard bioassays, described herein (see, e.g., Matsunaga et al. (1989) *Peptides* 10:349–354; Hardley et al. (1987) *Life Sci.* 40:1139–1145, herein incorporated by reference). These studies have concluded that the minimal sequence needed to elicit an equipotent response to the native MCH is MCH(5–15), a structure which lacks residues 1–4 from the N-terminal end, and residues 16–17 of the C-terminal end of the peptide. The removal of $Trp^{15}$, producing a fragment MCH(5–14), results in an analog 100 to 300 less active than native MCH indicating that Trp at position 15 is important for maintenance of full (equipotent) agonist activity of MCH, and that indole ring of Trp residue may be important in aiding the fit of MCH into its receptor pocket, thus facilitating binding. Because fragment analogs, which are N terminal deleted, e.g., those lacking residues 1–4, are equipotent to native MCH, they appear to not be required for MCH activity. The same was concluded for residues 16–17 in the C-terminal end of the peptide.

Furthermore, other investigators have synthesized MCH analogs with contracted ring structure and have tested them for activity in teleost fish skin bioassay (see, e.g., Lebl et al. (1988) *J. Med. Chem.* 31:949–954; Lebl et al. (1989) *Life Sci.* 44:451–457; Matsunaga et al. (1989) *Peptides* 10:349–354, herein incorporated by reference). The following ring contraction analogs (which retain a disulfide bond) were synthesized: [$Ala^5$, $Cys^{10}$]MCH, [$Ala^5$, $Cys^8$]MCH, [$Ala^5$, $Cys^7$]MCH, [$Ala^5$, $Cys^{10}$]$MCH_{5-17}$, [$Ala^5$, $Cys^8$]$MCH_{5-17}$, [$Ala^5$, $Cys^7$]$MCH_{5-17}$, [$Cys^{10}$]$MCH_{10-17}$, [$Cys^8$]$MCH_{8-17}$, and [$Cys^7$]$MCH_{7-17}$. The studies with these analogs have concluded that the disulfide bond between positions 5 and 14 is essential for the MCH-like activity, because ring contractions eliminated or greatly reduced the MCH-like activity. It seems that the 10 ring residue structure, MCH(5–14) is very important for optimal activation. Surprisingly, two of the analogs, [Ala$^5$, Cys$^8$]MCH$_{5-17}$ and [Cys$^{10}$]MCH$_{10-17}$, were found to be full agonists, however, with very reduced potency, indicating that the shortest sequence having MCH-like activity may be comprised of residues 10–14 (Val—Tyr—Arg—Pro—Cys) (SEQ ID NO:1) with residues at positions 11–14 (Tyr—Arg—Pro—Cys) (SEQ ID NO:2) possibly being crucial for message transduction.

In addition, acyclic analogs have been synthesized and tested for MCH activity in teleost fish skin bioassay (see, e.g., Kawauchi and Kawazoe (1988) *Advances in Pigment Cell Res.* 517–527; Matsunaga et al. (1992) *Life Sci.* 51:679–685, herein incorporated by reference). These analogs were constructed so that they differed form native MCH only in the polarity of the side chain group at positions 5 and 14. For one analog polar L-serine was substituted for cysteine at positions 5 and 14 (L-Ser$^{5,14}$ MCH), while for the other analog, non-polar L α-aminobutyrate (Abu) was substituted at the same positions (Abu$^{5,14}$ MCH). Another acyclic analog was constructed by reduction of the disulfide bond, followed by subsequent carboxymethylation of Cys residues at positions 5 and 14 (CAM-Cys$^{5,14}$ MCH). All of these analogs exhibited no MCH-like activity, suggesting that the disulfide bridge is necessary to maintain correct conformation and topographical features of MCH for receptor binding and transmembrane signal transduction.

MCH derivatives with modified residues have also been synthesized and tested for activity in fish scale assay (see, e.g., Kawauchi and Kawazoe (1988) *Advances in Pigment Cell Res.* 517–527, herein incorporated by reference). The following derivatives have been synthesized and tested for activity: NPS-Trp$^{15}$MCH, DHCH-Arg$^{4,9,12}$MCH, NO$_2$-Tyr$^{11}$MCH and S—O—Met$^{3,6}$MCH. Modifications of amino acid residues outside of the ring structure had no effect on the MCH activity, while the modifications of residues within the ring, e.g., DHCH-Arg$^{4,9,12}$MCH, NO$_2$-Tyr$^{11}$MCH and S—O—Met$^{3,6}$MCH, resulted in analogs with greatly reduced MCH activity. These results support the suggestion that the MCH activity is elicited from the cyclic segment (MCH5–14) of the peptide.

The melanocyte-based assays predict that peptides of the following structure will be useful as agonists of MCH activity:

R$^1$—R$^2$—R$^3$—R$^4$—R$^5$—R$^6$—R$^7$—R$^8$—R$^9$—R$^{10}$—R$^{11}$—R$^{12}$—R$^{13}$—R$^{14}$—R$^{15}$—R$^{16}$—R$^{17}$—R$^{18}$—R$^{19}$ (SEQ ID NO:3)

wherein:

R$^1$ is Asp, a conserved amino acid substitution from the table provided herein, any D amino acid, or deleted;

R$^2$ is Phe, a conserved amino acid substitution from the table provided herein, any D amino acid, or deleted;

R$^3$ is Asp, a conserved amino acid substitution from the table provided herein, any D amino acid, or deleted;

R$^4$ is Met or a conserved amino acid substitution from the table provided herein, Thr or a conserved amino acid substitution from the table provided herein, any D amino acid, or deleted;

R$^5$ is Leu or a conserved amino acid substitution from the table provided herein, Met or a conserved amino acid substitution from the table provided herein, any D amino acid, or deleted;

R$^6$ is Arg, a conserved amino acid substitution from the table provided herein, any D amino acid, deleted, or Cys;

R$^7$ is Cys, or any amino acid;

R$^8$ is Met, a conserved amino acid substitution from the table provided herein, or Cys;

R$^9$ is Leu or a conserved amino acid substitution from the table provided herein, or Val or a conserved amino acid substitution from the table provided herein;

R$^{10}$ is Gly, or a conserved amino acid substitution from the table provided herein;

R$^{11}$ is Arg, or a conserved amino acid substitution from the table provided herein;

R$^{12}$ is Val, or a conserved amino acid substitution from the table provided herein;

R$^{13}$ is Tyr, or a conserved amino acid substitution from the table provided herein;

R$^{14}$ is Arg, or a conserved amino acid substitution from the table provided herein;

R$^{15}$ is Pro, a conserved amino acid substitution from the table provided herein, or Cys;

R$^{16}$ is Cys, or any amino acid;

R$^{17}$ is Trp, a conserved amino acid substitution form the table provided herein, an analog of Trp, e.g., NPS-Trp, an amino acid having an aromatic side group, or Cys;

R$^{18}$ is Gln or a conserved amino acid substitution from the table provided herein, Glu or a conserved amino acid substitution from the table provided herein, Trp or a conserved amino acid substitution form the table provided herein, an analog of Trp, e.g., NPS-Trp, an amino acid having an aromatic side group, or deleted;

R$^{19}$ is Val, a conserved amino acid substitution from the table provided herein, or deleted;

provide that: if R$^6$ is Cys, then R$^{15}$ is Cys, the disulfide bridge is formed between the two, and R$^7$, R$^8$, R$^{16}$ and R$^{17}$ are not Cys; if R$^7$ is Cys, then R$^{16}$ is Cys, the disulfide bridge is formed between the two, and R$^6$, R$^8$, R$^{15}$ and R$^{17}$ are not Cys; if R$^8$ is Cys, then R$^{17}$ is Cys, the disulfide bridge is formed between the two, R$^6$, R$^7$, R$^{15}$ and R$^{16}$ are not Cys, and R$^{18}$ is Trp or a conserved amino acid substitution form the table provided herein, an analog of Trp, e.g., NPS-Trp, or an amino acid having an aromatic side group.

In preferred embodiments: R$^{12}$ is Val, R$^{13}$ is Tyr, R$^{14}$ is Arg, R$^{15}$ is Pro, R$^{16}$ is Cys and R$^{17}$ is Trp; the agonist has a disulfide bridge between residues R$^7$ and R$^{16}$; the disulfide ring includes ten amino acids; the agonist is deleted for any or all of the residues between R$^1$ and R$^6$; the agonist is deleted for one or both of the residues between R$^{18}$ and R$^{19}$; the agonist has at least 70, 80, or 90% homology with human, rat or salmon MCH; the agonist has 1, 2, 3, 4, 5 or more residues within the ring modified or substituted with a conserved amino acid from the table provided herein.

In preferred embodiments, the agonist is: MCH(2–19), MCH(3–19), MCH(4–19), MCH(5–19), MCH(6–19), MCH (7–19), MCH(1–18), MCH(2–18), MCH(3–18), MCH (4–18), MCH(5–18), MCH(6–18), MCH(7–18), MCH (1–17), MCH(2–17), MCH(3–17), MCH(4–17), MCH (5–17), MCH(6–17), MCH(7–17), and NPS-Trp$^{17}$MCH.

The melanocyte-based assays predict that the peptides of the following structure will be useful as antagonists of MCH activity:

R$^1$—R$^2$—R$^3$—R$^4$—R$^5$—R$^6$—R$^7$—R$^8$—R$^9$—R$^{10}$—R$^{11}$—R$^{12}$—R$^{13}$—R$^{14}$—R$^{15}$—R$^{16}$—R$^{17}$—R$^{18}$—R$^{19}$ (SEQ ID NO:3)

wherein:

R$^1$ is Asp, a conserved amino acid substitution from the table provided herein, any D amino acid, or deleted;

R$^2$ is Phe, a conserved amino acid substitution from the table provided herein, any D amino acid, or deleted;

$R^3$ is Asp, a conserved amino acid substitution from the table provided herein, any D amino acid, or deleted;

$R^4$ is Met or a conserved amino acid substitution from the table provided herein, Thr or a conserved amino acid substitution from the table provided herein, any D amino acid, or deleted;

$R^5$ is Leu or a conserved amino acid substitution from the table provided herein, Met or a conserved amino acid substitution from the table provided herein, any D amino acid, or deleted;

$R^6$ is Arg, a conserved amino acid substitution from the table provided herein, any D amino acid, deleted, or Cys;

$R^7$ is Cys, or any amino acid;

$R^8$ is Met, a conserved amino acid substitution from the table provided herein, or Cys;

$R^9$ is Leu or a conserved amino acid substitution from the table provided herein, or Val or a conserved amino acid substitution from the table provided herein;

$R^{10}$ is Gly, or a conserved amino acid substitution from the table provided herein;

$R^{11}$ is Arg, or a conserved amino acid substitution from the table provided herein;

$R^{12}$ is any amino acid other than Val, or other than a conserved amino acid replacement;

$R^{13}$ is any amino acid other than Tyr, or other than a conserved amino acid replacement;

$R^{14}$ is any amino acid other than Arg, or other than a conserved amino acid replacement;

$R^{15}$ is any amino acid other than Pro, other than a conserved amino acid replacement, or Cys;

$R^{16}$ is Cys, or any other amino acid;

$R^{17}$ is Trp or a conserved amino acid substitution form the table provided herein, an analog of Trp, e.g., NPS-Trp, an amino acid having an aromatic side group, any amino acid other than Trp, other than a conserved amino acid replacement, an amino acid lacking an aromatic side group, deleted, or Cys;

$R^{18}$ is Gln or a conserved amino acid substitution from the table provided herein, Glu or a conserved amino acid substitution from the table provided herein, Trp or a conserved amino acid substitution form the table provided herein, an analog of Trp, e.g., NPS-Trp, an amino acid having an aromatic side group, any amino acid other than Trp, other than a conserved amino acid replacement, an amino acid lacking an aromatic side group, or deleted;

$R^{19}$ is Val, a conserved amino acid substitution from the table provided herein, or deleted;

provided that: if $R^6$ is Cys, then $R^{15}$ is Cys, the disulfide bridge is formed between the two, and $R^7$, $R^8$, $R^{16}$ and $R^{17}$ are not Cys; if $R^7$ is Cys, then $R^{16}$ is Cys, the disulfide bridge is formed between the two, and $R^6$, $R^8$, $R^{15}$ and $R^{17}$ are not Cys; if $R^8$ is Cys, then $R^{17}$ is Cys, the disulfide bridge is formed between the two, $R^6$, $R^7$, $R^{15}$ and $R^{16}$ are not Cys, and $R^{18}$ is Trp or a conserved amino acid substitution form the table provided herein, an analog of Trp, e.g., NPS-Trp, an amino acid having an aromatic side group, any amino acid other than Trp, other than a conserved amino acid replacement, an amino acid lacking an aromatic side group, or deleted.

In preferred embodiments:

$R^{12}$ is any amino acid other than Val, or other than a conserved amino acid replacement;

$R^{13}$ is any amino acid other than Tyr, or other than a conserved amino acid replacement;

$R^{14}$ is any amino acid other than Arg, or other than a conserved amino acid replacement;

$R^{15}$ is any amino acid other than Pro, or other than a conserved amino acid replacement;

$R^{16}$ is Cys;

$R^{17}$ is any amino acid other than Trp, other than a conserved amino acid replacement, an amino acid lacking an aromatic side group, or deleted.

In preferred embodiments: the antagonist has a disulfide bridge between residues $R^7$ and $R^{16}$; the disulfide ring includes ten amino acids; the antagonist is deleted for any or all of the residues between $R^1$ and $R^6$; the antagonist is deleted for one or both of the residues between $R^{18}$ and $R^{19}$; the antagonist has at least 70, 80, or 90% homology with human, rat or salmon MCH; the agonist has 1, 2, 3, 4, 5 or more residues within the ring modified or substituted with a nonconserved amino acid.

In preferred embodiments, the antagonist is: MCH(1–16), MCH(2–16), MCH(3–16), MCH(4–16), MCH(5–16), MCH(6–16), MCH(7–16), DHCH-Arg$^{6,11,14}$MCH, and NO$_2$—Tyr$^{13}$MCH.

TRANSGENIC ANIMALS

The invention includes transgenic animals which include cells (of that animal) which contain an MHC transgene and which preferably express (or misexpress) an endogenous or exogenous MCH in one or more cells in the animal. The MCH transgene can encode the wild-type form of the protein, or can encode homologs thereof, including both agonists and antagonists, as well as antisense constructs. In preferred embodiments, the expression of the transgene is restricted to specific subsets of cells, or tissues, e.g., hypothalamus, utilizing, for example, cis-acting sequences that control expression in the desired pattern. Tissue-specific regulatory sequences and conditional regulatory sequences can be used to control expression of the transgene in certain spatial patterns. Temporal patterns of expression can be provided by, for example, conditional recombination systems or prokaryotic transcriptional regulatory sequences.

Genetic techniques which allow for the expression of transgenes, that are regulated in vivo via site-specific genetic manipulation, are known to those skilled in the art. For example, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of the subject MCH polypeptide. For example, excision of a target sequence which interferes with the expression of a recombinant MCH gene, such as one which encodes an antagonistic homolog, can be designed to activate expression of that gene. This interference with expression of the protein can result from a variety of mechanisms, such as spatial separation of the MCH gene from the promoter element or an internal stop codon. Moreover, the transgene can be made wherein the coding sequence of the gene is flanked recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

See e.g., descriptions of the crelloxP recombinase system of bacteriophage PI (Lakso et al. (1992) *PNAS* 89:6232–6236; Orban et al. (1992) *PNAS* 89:6861–6865) or the FLP recombinase system of *Saccharomyces cerevisiae* (O'Gorman et al. (1991) *Science* 251:1351–1355; PCT publication WO 92/15694).

Genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of the recombinant MCH can be regulated via control of recombinase expression.

Similar conditional transgenes can be provided using prokaryotic promoter sequences which require prokaryotic proteins to be simultaneous expressed in order to facilitate expression of the transgene. Exemplary promoters and the corresponding trans-activating prokaryotic proteins are given in U.S. Pat. No. 4,833,080. Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, the MCH transgene could remain silent into adulthood until "turned on" by the introduction of the trans-activator.

GENE THERAPY

The gene constructs of the invention can also be used as a part of a gene therapy protocol to deliver nucleic acids encoding either an agonistic or antagonistic form of an MCH peptide. The invention features expression vectors for in vivo transfection and expression of an MCH peptide in particular cell types so as to reconstitute the function of, or alternatively, antagonize the function of MCH peptide in a cell in which that peptide is misexpressed. Expression constructs of MCH peptides, may be administered in any biologically effective carrier, e.g. any formulation or composition capable of effectively delivering the MCH gene to cells in vivo. Approaches include insertion of the subject gene in viral vectors including recombinant retroviruses, adenovirus, adeno-associated virus, and herpes simplex virus- 1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo.

A preferred approach for in vivo introduction of nucleic acid into a cell is by use of a viral vector containing nucleic acid, e.g. a cDNA, encoding an MCH polypeptide. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, A. D. (1990) *Blood* 76:271). A replication defective retrovirus can be packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ΨCrip, ΨCre, Ψ2 and ΨAm. Retroviruses have been used to introduce a variety of genes into many different cell types, including epithelial cells, in vitro and/or in vivo (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad. Sci. USA* 88:8039–8043; Ferry et al. (1991) *Proc. Natl. Acad. Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad Sci. USA* 89:10892–10895; Hwu et al. (1993) *J. Immunol.* 150:4104–4115; U.S. Pat. Nos. 4,868,116; 4,980,286; PCT Application WO 89/07136; PCT Application WO 89/02468; PCT Application WO 89/05345; and PCT Application WO 92/07573).

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See, for example, Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 dl324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells (Rosenfeld et al. (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267).

Yet another viral vector system useful for delivery of the subject MCH gene is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). It is also one of the few viruses that may integrate its DNA into non-dividing cells, and exhibits a high frequency of stable integration (see for example Flotte et al. (1992) *Am. J Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J. Virol.* 51:611–619; and Flotte et al. (1993) *J. Biol. Chem.* 268:3781–3790).

In addition to viral transfer methods, such as those illustrated above, non-viral methods can also be employed to cause expression of an MCH peptide in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject MCH gene by the targeted cell. Exemplary gene delivery systems of this type include liposomal derived systems, poly-lysine conjugates, and artificial viral envelopes.

In a representative embodiment, a gene encoding an MCH polypeptide can be entrapped in liposomes bearing positive charges on their surface (e.g., lipofectins) and (optionally) which are tagged with antibodies against cell surface antigens of the target tissue (Mizuno et al. (1992) *No Shinkei Geka* 20:547–551; PCT publication WO91/06309; Japanese patent application 1047381; and European patent publication EP-A-43075).

In clinical settings, the gene delivery systems for the therapeutic MCH gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by Stereotactic injection (e.g. Chen et al. (1994) *PNAS* 91:3054–3057).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced in tact from recombinant cells, e.g. retroviral vectors, the pharmaceutical preparation can comprise one or more cells which produce the gene delivery system.

ANTISENSE THERAPY

Another aspect of the invention relates to the use of the isolated nucleic acid in "antisense" therapy. As used herein, "antisense" therapy refers to administration or in situ generation of oligonucleotides or their derivatives which specifically hybridizes (e.g. binds) under cellular conditions, with the cellular mRNA and/or genomic DNA encoding MCH so as to inhibit expression of the encoded protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes an MCH. Alternatively, the antisense construct is an oligonucleotide probe which is generated ex vivo and which, when introduced into the cell causes inhibition of expression by hybridizing with the mRNA and/or genomic sequences of an MCH gene. Such oligonucleotide probes are preferably modified oligonucleotide which are resistant to endogenous nucleases, e.g. exonucleases and/or endonucleases, and is therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) *Biotechniques* 6:958 976; and Stein et al. (1988) *Cancer Res* 48:2659–2668.

Accordingly, the modified oligomers of the invention are useful in therapeutic, diagnostic, and research contexts. In therapeutic applications, the oligomers are utilized in a manner appropriate for antisense therapy in general. For such therapy, the oligomers of the invention can be formulated for a variety of loads of administration, including systemic and topical or localized administration. For systemic administration, injection is preferred, including intramuscular, intravenous, intraperitoneal, and subcutaneous for injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included in the invention.

The compounds can be administered orally, or by transmucosal or transdermal means. For transmucosal or transdermal administration, penetrants appropriate to the barrier to be permeated are used in the formulation. Such penetrants are known in the art, and include, for example, for transmucosal administration bile salts and fusidic acid derivatives, and detergents. Transmucosal administration may be through nasal sprays or using suppositories. For oral administration, the oligomers are formulated into conventional oral administration forms such as capsules, tablets, and tonics. For topical administration, the oligomers of the invention are formulated into ointments, salves, gels, or creams as known in the art.

In addition to use in therapy, the oligomers of the invention may be used as diagnostic reagents to detect the presence or absence of the target DNA or RNA sequences to which they specifically bind.

PRODUCTION OF FRAGMENTS AND ANALOGS

The inventor has discovered that MCH regulates eating behavior. Because structure of MCH is known, one skilled in the art can alter the MCH structure, e.g., by producing fragments or analogs, and test the newly produced structures for activity. Examples of prior art methods which allow the production and testing of fragments and analogs are discussed herein. These, or analogous methods can be used to make and screen fragments and analogs of MCH that bind to naturally occurring ligand of MCH, e.g., an MCH receptor, e.g., MC3-R. Likewise they can be used to make fragments and analogs that will bind MCH.

GENERATION OF FRAGMENTS

Fragments of a protein can be produced in several ways, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Expression of the mutagenized DNA produces polypeptide fragments. Digestion with "end-nibbling" endonucleases can thus generate DNA's which encode an array of fragments. DNA's which encode fragments of a protein can also be generated by random shearing, restriction digestion or a combination of the above-discussed methods.

Fragments can also be chemically synthesized using techniques known in the art such as conventional Merrifield solid phase f-Moc or t-Boc chemistry. For example, peptides of the present invention may be arbitrarily divided into fragments of desired length with no overlap of the fragments, or divided into overlapping fragments of a desired length.

PRODUCTION OF ALTERED DNA AND PEPTIDE SEQUENCES: RANDOM METHODS

Amino acid sequence variants of a protein can be prepared by random mutagenesis of DNA which encodes a protein or a particular domain or region of a protein. Useful methods include PCR mutagenesis and saturation mutagenesis. A library of random amino acid sequence variants can also be generated by the synthesis of a set of degenerate oligonucleotide sequences. (Methods for screening proteins in a library of variants are elsewhere herein.)

PCR Mutagenesis

In PCR mutagenesis, reduced Taq polymerase fidelity is used to introduce random mutations into a cloned fragment of DNA (Leung et al., 1989, *Technique* 1:1 1–15). This is a very powerful and relatively rapid method of introducing random mutations. The DNA region to be mutagenized is amplified using the polymerase chain reaction (PCR) under conditions that reduce the fidelity of DNA synthesis by Taq DNA polymerase, e.g., by using a dGTP/dATP ratio of five and adding $Mn^{2+}$ to the PCR reaction. The pool of amplified DNA fragments are inserted into appropriate cloning vectors to provide random mutant libraries.

Saturation Mutagenesis

Saturation mutagenesis allows for the rapid introduction of a large number of single base substitutions into cloned DNA fragments (Mayers et al., 1985, *Science* 229:242). This technique includes generation of mutations, e.g., by chemical treatment or irradiation of single-stranded DNA in vitro, and synthesis of a complimentary DNA strand. The mutation frequency can be modulated by modulating the severity of the treatment, and essentially all possible base substitutions can be obtained. Because this procedure does not involve a genetic selection for mutant fragments both neutral substitutions, as well as those that alter function, are obtained. The distribution of point mutations is not biased toward conserved sequence elements.

Degenerate Oligonucleotides

A library of homologs can also be generated from a set of degenerate oligonucleotide sequences. Chemical synthesis of a degenerate sequences can be carried out in an automatic DNA synthesizer, and the synthetic genes then ligated into an appropriate expression vector. The synthesis of degenerate oligonucleotides is known in the art (see for example, Narang, S A (1983) *Tetrahedron* 39:3; Itakura et al. (1981) *Recombinant DNA, Proc 3rd Cleveland Sympos. Macromolecules,* ed. A G Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249:404–406; Cwirla et al. (1990) *PNAS* 87:6378–6382; as well as U.S. Pat. Nos. 5,223,409, 5,198, 346, and 5,096,815).

PRODUCTION OF ALTERED DNA AND PEPTIDE SEQUENCES: METHODS FOR DIRECTED MUTAGENESIS

Non-random or directed, mutagenesis techniques can be used to provide specific sequences or mutations in specific regions. These techniques can be used to create variants which include, e.g., deletions, insertions, or substitutions, of residues of the known amino acid sequence of a protein. The sites for mutation can be modified individually or in series, e.g., by (1) substituting first with conserved amino acids and then with more radical choices depending upon results achieved, (2) deleting the target residue, or (3) inserting residues of the same or a different class adjacent to the located site, or combinations of options 1–3.

Alanine Scanning Mutagenesis

Alanine scanning mutagenesis is a useful method for identification of certain residues or regions of the desired protein that are preferred locations or domains for mutagenesis, Cunningham and Wells (*Science* 244:1081–1085, 1989). In alanine scanning, aresidue or group of target residues are identified (e.g., charged residues such as Arg, Asp, His, Lys, and Glu) and replaced by a neutral or negatively charged amino acid (most preferably alanine or polyalanine). Replacement of an amino acid can affect the interaction of the amino acids with the surrounding aqueous environment in or outside the cell. Those domains demonstrating functional sensitivity to the substitutions are then refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis may be conducted at the target codon or region and the expressed desired protein subunit variants are screened for the optimal combination of desired activity.

Oligonucleotide-Mediated Mutagenesis

Oligonucleotide-mediated mutagenesis is a useful method for preparing substitution, deletion, and insertion variants of DNA, see, e.g., Adelman et al., (*DNA* 2:183, 1983). Briefly, the desired DNA is altered by hybridizing an oligonucleotide encoding a mutation to a DNA template, where the template is the single-stranded form of a plasmid or bacteriophage containing the unaltered or native DNA sequence of the desired protein. After hybridization, a DNA polymerase is used to synthesize an entire second complementary strand of the template that will thus incorporate the oligonucleotide primer, and will code for the selected alteration in the desired protein DNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. Natl. Acad. Sci. USA*, 75:5765[1978]).

Cassette Mutagenesis

Another method for preparing variants, cassette mutagenesis, is based on the technique described by Wells et al. (*Gene*, 34:315[1985]). The starting material is a plasmid (or other vector) which includes the protein subunit DNA to be mutated. The codon(s) in the protein subunit DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the desired protein subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are comparable with the ends of the linearized plasmid, such that it can be directly ligated to the plasmid. This plasmid now contains the mutated desired protein subunit DNA sequence.

Combinatorial Mutagenesis

Combinatorial mutagenesis can also be used to generate mutants (Ladner et al., WO 88/06630). In this method, the amino acid sequences for a group of homologs or other related proteins are aligned, preferably to promote the highest homology possible. All of the amino acids which appear at a given position of the aligned sequences can be selected to create a degenerate set of combinatorial sequences. The variegated library of variants is generated by combinatorial mutagenesis at the nucleic acid level, and is encoded by a variegated gene library. For example, a mixture of synthetic oligonucleotides can be enzymatically ligated into gene sequences such that the degenerate set of potential sequences are expressible as individual peptides, or alternatively, as a set of larger fusion proteins containing the set of degenerate sequences.

PRIMARY HIGH-THROUGH-PUT METHODS FOR SCREENING LIBRARIES OF PEPTIDE FRAGMENTS OF HOMOLOGS

Various techniques are known in the art for screening generated mutant gene products. Techniques for screening large gene libraries often include cloning the gene library into replicable expression vectors, transforming appropriate cells with the resulting library of vectors, and expressing the genes under conditions in which detection of a desired activity, e.g., in this case, binding to MCH or naturally occuring ligand of MCH, e.g., an MCH receptor, e.g., MC3-R, facilitates relatively easy isolation of the vector encoding the gene whose product was detected. Each of the techniques described below is amenable to high through-put analysis for screening large numbers of sequences created, e.g., by random mutagenesis techniques.

Two Hybrid Systems

Two hybrid assays (as with the other screening methods described herein), can be used to identify fragments or analogs of a MCH polypeptide which binds to naturally occuring ligand of MCH, e.g., an MCH receptor, e.g., MC3-R. These may include agonists, superagonists, and antagonists. (The MCH ligand is used as the bait protein and the library of variants are expressed as fish fusion proteins.) In an analogous fashion, a two hybrid assay (as with the other screening methods described herein), can be used to find fragments and analogs which bind to MCH.

Display Libraries

In one approach to screening assays, the candidate peptides are displayed on the surface of a cell or viral particle, and the ability of particular cells or viral particles to bind an appropriate receptor protein via the displayed product is detected in a "panning assay". For example, the gene library can be cloned into the gene for a surface membrane protein of a bacterial cell, and the resulting fusion protein detected by panning (Ladner et al., WO 88/06630; Fuchs et al. (1991) *Bio/Technology* 9:1370–1371; and Goward et al. (1992) *TIBS* 18:136–140). In a similar fashion, a detectably labeled ligand can be used to score for potentially functional peptide homologs. Fluorescently labeled ligands, e.g., receptors, can be used to detect homolog which retain ligand-binding activity. The use of fluorescently labeled ligands, allows cells to be visually inspected and separated under a fluorescence microscope, or, where the morphology of the cell permits, to be separated by a fluorescence-activated cell sorter.

A gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at concentrations well over $10^{13}$ phage per milliliter, a large number of phage can be screened at one time. Second, since each infectious phage displays a gene product on its surface, if a particular phage is recovered from an affinity matrix in low yield, the phage can be amplified by another round of infection. The group of almost identical *E. coli* filamentous phages M13, fd., and f1 are most often used in phage display libraries. Either of the phage gIII or gVIII coat proteins can be used to generate fusion proteins without disrupting the ultimate packaging of the viral particle. Foreign epitopes can be expressed at the $NH_2$-terminal end of pIII and phage bearing such epitopes recovered from a large excess of phage lacking this epitope (Ladner et al. PCT publication WO 90/02909; Garrard et al., PCT publication WO 92/09690; Marks et al. (1992) *J. Biol. Chem.* 267:16007–16010; Griffiths et al. (1993) *EMBO J* 12:725–734; Clackson et al. (1991) *Nature* 352:624–628; and Barbas et al. (1992) *PNAS* 89:4457–4461).

A common approach uses the maltose receptor of *E. coli* (the outer membrane protein, LamB) as a peptide fusion partner (Charbit et al. (1986) *EMBO* 5, 3029–3037). Oligonucleotides have been inserted into plasmids encoding the LamB gene to produce peptides fused into one of the extracellular loops of the protein. These peptides are available for binding to ligands, e.g., to antibodies, and can elicit an immune response when the cells are administered to animals. Other cell surface proteins, e.g., OmpA (Schorr et al. (1991) *Vaccines* 91, pp. 387–392), PhoE (Agterberg, et al. (1990) *Gene* 88, 37–45), and PAL (Fuchs et al. (1991) *Bio/Tech* 9, 1369–1372), as well as large bacterial surface structures have served as vehicles for peptide display. Peptides can be fused to pilin, a protein which polymerizes to form the pilus-a conduit for interbacterial exchange of genetic information (Thiry et al. (1989) *Appl. Environ. Microbiol.* 55, 984–993). Because of its role in interacting with other cells, the pilus provides a useful support for the presentation of peptides to the extracellular environment. Another large surface structure used for peptide display is the bacterial motive organ, the flagellum. Fusion of peptides to the subunit protein flagellin offers a dense array of may peptides copies on the host cells (Kuwajima et al. (1988) *Bio/Tech.* 6, 1080–1083). Surface proteins of other bacterial species have also served as peptide fusion partners. Examples include the Staphylococcus protein A and the outer membrane protease IgA of Neisseria (Hansson et al. (1992) *J. Bacteriol.* 174, 4239–4245 and Klauser et al. (1990) *EMBO J.* 9, 1991–1999).

In the filamentous phage systems and the LamB system described above, the physical link between the peptide and its encoding DNA occurs by the containment of the DNA within a particle (cell or phage) that carries the peptide on its surface. Capturing the peptide captures the particle and the DNA within. An alternative scheme uses the DNA-binding protein LacI to form a link between peptide and DNA (Cull et al. (1992) *PNAS USA* 89:1865–1869). This system uses a plasmid containing the LacI gene with an oligonucleotide cloning site at its 3'-end. Under the controlled induction by arabinose, a LacI-peptide fusion protein is produced. This fusion retains the natural ability of LacI to bind to a short DNA sequence known as LacO operator (LacO). By installing two copies of LacO on the expression plasmid, the LacI-peptide fusion binds tightly to the plasmid that encoded it. Because the plasmids in each cell contain only a single oligonucleotide sequence and each cell expresses only a single peptide sequence, the peptides become specifically and stably associated with the DNA sequence that directed its synthesis. The cells of the library are gently lysed and the peptide-DNA complexes are exposed to a matrix of immobilized receptor to recover the complexes containing active peptides. The associated plasmid DNA is then reintroduced into cells for amplification and DNA sequencing to determine the identity of the peptide ligands. As a demonstration of the practical utility of the method, a large random library of dodecapeptides was made and selected on a monoclonal antibody raised against the opioid peptide dynorphin B. A cohort of peptides was recovered, all related by a consensus sequence corresponding to a six-residue portion of dynorphin B. (Cull et al. (1992) *Proc. Natl. Acad. Sci. U.S.A.* 89–1869)

This scheme, sometimes referred to as peptides-on-plasmids, differs in two important ways from the phage display methods. First, the peptides are attached to the C-terminus of the fusion protein, resulting in the display of the library members as peptides having free carboxy termini. Both of the filamentous phage coat proteins, pIII and pVIII, are anchored to the phage through their C-termini, and the guest peptides are placed into the outward-extending N-terminal domains. In some designs, the phage-displayed peptides are presented right at the amino terminus of the fusion protein. (Cwirla, et al. (1990) *Proc. Natl. Acad. Sci. U.S.A.* 87, 6378–6382) A second difference is the set of biological biases affecting the population of peptides actually present in the libraries. The LacI fusion molecules are confined to the cytoplasm of the host cells. The phage coat fusions are exposed briefly to the cytoplasm during translation but are rapidly secreted through the inner membrane into the periplasmic compartment, remaining anchored in the membrane by their C-terminal hydrophobic domains, with the N-termini, containing the peptides, protruding into the periplasm while awaiting assembly into phage particles. The peptides in the LacI and phage libraries may differ significantly as a result of their exposure to different proteolytic activities. The phage coat proteins require transport across the inner membrane and signal peptidase processing as a prelude to incorporation into phage. Certain peptides exert a deleterious effect on these processes and are underrepresented in the libraries (Gallop et al. (1994) *J. Med Chem.* 37(9):1233–1251). These particular biases are not a factor in the LacI display system.

The number of small peptides available in recombinant random libraries is enormous. Libraries of $10^7$–$10^9$ independent clones are routinely prepared. Libraries as large as $10^{11}$ recombinants have been created, but this size approaches the practical limit for clone libraries. This limitation in library size occurs at the step of transforming the DNA containing randomized segments into the host bacterial cells. To circumvent this limitation, an in vitro system based on the display of nascent peptides in polysome complexes has recently been developed. This display library method has the potential of producing libraries 3–6 orders of magnitude larger than the currently available phage/phagemid or plasmid libraries. Furthermore, the construction of the libraries, expression of the peptides, and screening, is done in an entirely cell-free format.

In one application of this method (Gallop et al. (1994) *J. Med. Chem.* 37(9):1233–1251), a molecular DNA library encoding $10^{12}$ decapeptides was constructed and the library expressed in an *E. coli* S30 in vitro coupled transcription/translation system. Conditions were chosen to stall the ribosomes on the mRNA, causing the accumulation of a substantial proportion of the RNA in polysomes and yielding complexes containing nascent peptides still linked to their encoding RNA. The polysomes are sufficiently robust to be affinity purified on immobilized receptors in much the same way as the more conventional recombinant peptide display libraries are screened. RNA from the bound complexes is recovered, converted to cDNA, and amplified by PCR to produce a template for the next round of synthesis and screening. The polysome display method can be coupled to the phage display system. Following several rounds of screening, cDNA from the enriched pool of polysomes was cloned into a phagemid vector. This vector serves as both a peptide expression vector, displaying peptides fused to the coat proteins, and as a DNA sequencing vector for peptide identification. By expressing the polysome-derived peptides on phage, one can either continue the affinity selection procedure in this format or assay the peptides on individual clones for binding activity in a phage ELISA, or for binding specificity in a completion phage ELISA (Barret, et al. (1992) *Anal. Biochem.* 204,357–364). To identify the sequences of the active peptides one sequences the DNA produced by the phagemid host.

SECONDARY SCREENS

The high through-put assays described above can be followed by secondary screens in order to identify further biological activities which will, e.g., allow one skilled in the art to differentiate agonists from antagonists. The type of a secondary screen used will depend on the desired activity that needs to be tested (some of the assays which test specific MCH activity have been described above). For example, an assay can be developed in which the ability to inhibit an interaction between a protein of interest and its respective ligand can be used to identify antagonists from a group of peptide fragments isolated though one of the primary screens described above.

Therefore, methods for generating fragments and analogs and testing them for activity are known in the art. Once the core sequence of interest is identified, it is routine to perform for one skilled in the art to obtain analogs and fragments.

PEPTIDE MIMETICS

The invention also provides for reduction of the protein binding domains of the MCH peptide, to generate mimetics, e.g. peptide or non-peptide agents, which are able to disrupt binding, in this case, of an MCH with a naturally occurring ligand of MCH, e.g., an MCH receptor, e.g., MC3-R. The critical residues of the MCH peptide which are involved in molecular recognition of MCH ligand can be determined and used to generate MCH-derived peptidomimetics which competitively or non-competatively inhibit binding of the MCH with an MCH ligand (see, for example, "Peptide inhibitors of human papillomavirus protein binding to retinoblastoma gene protein" European patent applications EP-412,762A and EP-B31,080A). By employing, for example, scanning mutagenesis to map the amino acid residues of a particular MCH peptide involved in binding the MCH ligand, peptidomimetic compounds (e.g. diazepine or isoquinoline derivatives) can be generated which mimic those residues in binding to an MCH ligand, and which therefore can inhibit binding of the MCH to the ligand and thereby interfere with the function of MCH. For instance, non-hydrolyzable peptide analogs of such residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gama lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J Med Chem 29:295; and Ewenson et al. in Peptides: Structure and Function (Proceedings of the 9th American Peptide Symposium) Pierce Chemical Co. Rockland, Ill., 1985), β-turn dipeptide cores (Nagai et al. (1985) Tetrahedron Lett 26:647; and Sato et al. (1986) J Chem Soc Perkin Trans 1:1231), and β-aminoalcohols (Gordon et al. (1985) Biochem Biophys Res Commun126:419; and Dann et al. (1986) Biochem Biophys Res Commun 134:71).

ADMINISTRATION

The compounds of the invention can be formulated to ensure proper distribution in vivo. For example, the blood-brain barrier (BBB) excludes many highly hydrophilic compounds. To ensure that the therapeutic compounds of the invention cross the BBB, they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs ("targeting moieties"), thus providing targeted drug delivery (see, e.g., V. V. Ranade (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J. Physiol. 1233:134); gp120 (Schreier et al. (1994) J. Biol. Chem. 269:9090); see also K. Keinanen; M. L. Laukkanen (1994) FEBS Lett. 346:123; J. J. Killion; I. J. Fidler (1994) Immunomethods 4:273. In a preferred embodiment, the therapeutic compounds of the invention are formulated in liposomes; in a more preferred embodiment, the liposomes include a targeting moiety.

To administer the therapeutic compound by other than parenteral administration, it may be necessary to coat the compound with, or co-administer the compound with, a material to prevent its inactivation. For example, the therapeutic compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., (1984) J. Neuroimmunol. 7:27).

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The vehicle can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

Appropriate dosages can be determined by prior art methods, but can be in the range of 0.001–100 mg/kg, or 0.1–10 mg/kg of body weight.

OTHER EMBODIMENTS

Analogs can differ from naturally occurring MCH in amino acid sequence or in ways that do not involve sequence, or both. Non-sequence modifications include in vivo or in vitro chemical derivatization of MCH. Non-sequence modifications include changes in acetylation, methylation, phosphorylation, carboxylation, or glycosylation.

Preferred analogs include MCH (or biologically active fragments thereof) whose sequences differ from the wild-type sequence by one or more conservative amino acid substitutions or by one or more non-conservative amino acid substitutions, deletions, or insertions which do not abolish the MCH biological activity. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative substitutions can be taken from the table below.

TABLE 1

CONSERVATIVE AMINO ACID REPLACEMENTS

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |

TABLE 1-continued

CONSERVATIVE AMINO ACID REPLACEMENTS

| For Amino Acid | Code | Replace with any of |
|---|---|---|
| Glycine | G | Ala, D-Ala, Pro, D-Pro, β-Ala Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other analogs within the invention are those with modifications which increase peptide stability; such analogs may contain, for example, one or more non-peptide bonds (which replace the peptide bonds) in the peptide sequence. Also included are: analogs that include residues other than naturally occurring L-amino acids, e.g., D-amino acids or non-naturally occurring or synthetic amino acids, e.g., β or γ amino acids; and cyclic analogs.

In order to obtain an MCH polypeptide, MCH-encoding DNA can be introduced into an expression vector, the vector introduced into a cell suitable for expression of the desired protein, and the peptide recovered and purified, by prior art methods. Antibodies to the peptides an proteins can be made by immunizing an animal, e.g., a rabbit or mouse, and recovering anti-MCH antibodies by prior art methods.

Other embodiments are within the following claims.

What is claimed is:

1. A method of promoting any of eating, the gain of weight, or maintenance of weight, in a subject comprising administering an effective amount of melanocyte concentrating hormone (MCH), or an agonist of MCH, wherein the agonist of MCH is a peptide analog having one to five amino acid residues which have been substituted with a conservative or a non-conservative amino acid residue or which have been deleted, to said subject thereby promoting any of eating, the gain of weight or maintenance of weight.

2. The method of claim 1, wherein said subject suffers from anorexia nervosa.

3. The method of claim 1, wherein said subject is currently or has been administered a treatment selected from the group consisting of chemotherapy, radiation therapy or dialysis.

4. The method of claim 1, wherein said subject suffers from AIDS, anorexia nervosa or renal disease.

5. The method of claim 1, wherein said subject is a human.

6. The method of claim 1, wherein said subject is administered a second dose of MCH, or of said agonist of MCH.

7. The method of claim 1, wherein said agonist of MCH has one amino acid residue substituted with a conservative or a non-conservative amino acid residue or deleted.

8. The method of claim 1, wherein MCH is administered to said subject.

9. The method of claim 1, wherein an agonist is administered to said subject.

10. The method of claim 1, wherein said agonist of MCH has two amino acid residues substituted with a conservative or a non-conservative amino acid residue or deleted.

11. The method of claim 1, wherein said agonist of MCH has three amino acid residues substituted with a conservative or a non-conservative amino acid residue or deleted.

12. The method of claim 1, wherein said agonist of MCH has four amino acid residues substituted with a conservative or a non-conservative amino acid residue or deleted.

13. The method of claim 1, wherein said agonist of MCH has five amino acid residues substituted with a conservative or a non-conservative amino acid residue or deleted.

14. The method of claim 1, wherein eating is promoted.

15. The method of claim 1, wherein the maintenance of weight is promoted.

16. The method of claim 1, wherein the gain of weight is promoted.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:1:

Val Tyr Arg Pro Cys
1               5

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:2:

Tyr Arg Pro Cys
1

( 2 ) INFORMATION FOR SEQ ID NO:3:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:3:

Xaa Xaa Xaa Xaa Xaa Xaa Xaa Xaa Xaa Xaa Xaa Xaa Xaa Xaa Xaa Xaa
1               5                   10                  15
Xaa Xaa Xaa